(12) United States Patent
Sugimoto et al.

(10) Patent No.: US 10,695,046 B2
(45) Date of Patent: *Jun. 30, 2020

(54) TISSUE ANCHOR AND ANCHORING SYSTEM

(71) Applicant: Edwards Lifesciences Corporation, Irvine, CA (US)

(72) Inventors: Hiroatsu Sugimoto, Cambridge, MA (US); Aaron M. Call, Mesa, AZ (US); Karl R. Leinsing, Dover, NH (US)

(73) Assignee: Edwards Lifesciences Corporation, Irvine, CA (US)

(*) Notice: Subject to any disclaimer, the term of this patent is extended or adjusted under 35 U.S.C. 154(b) by 179 days.

This patent is subject to a terminal disclaimer.

(21) Appl. No.: 15/680,742

(22) Filed: Aug. 18, 2017

(65) Prior Publication Data

US 2018/0028171 A1  Feb. 1, 2018

Related U.S. Application Data

(60) Continuation of application No. 14/581,264, filed on Dec. 23, 2014, now Pat. No. 9,814,454, which is a
(Continued)

(51) Int. Cl.
*A61B 17/04* (2006.01)
*A61B 17/00* (2006.01)

(52) U.S. Cl.
CPC .... *A61B 17/0401* (2013.01); *A61B 17/00234* (2013.01); *A61B 17/0469* (2013.01);
(Continued)

(58) Field of Classification Search
CPC ............ A61B 17/0469; A61B 17/0487; A61B 2017/0496; A61B 17/00234; A61B 17/0401
See application file for complete search history.

(56) References Cited

U.S. PATENT DOCUMENTS

| 2,143,910 A | 1/1939 | Didusch |
| 3,604,488 A | 9/1971 | Wishart et al. |

(Continued)

FOREIGN PATENT DOCUMENTS

| EP | 1016377 | 7/2000 |
| EP | 1034753 A1 | 9/2000 |

(Continued)

OTHER PUBLICATIONS

Cardiac Surgery Renaissance, Anatomical Landscape; Composite Profile of CABG and Valve Procedures, Apr. 25, 1996, Cardiology Roundtable Interviews.
(Continued)

*Primary Examiner* — Gregory A Anderson
(74) *Attorney, Agent, or Firm* — Thomas C. Richardson

(57) ABSTRACT

A tissue anchor includes an anchor member formed from a generally flexible material. An activation member, which may be a tensioning member, causes proximal and distal end portions of the anchor member to move toward each other into a shortened configuration suitable for anchoring against the tissue. The tissue anchor can optionally be deployed and activated using a catheter device.

19 Claims, 15 Drawing Sheets

Related U.S. Application Data continuation of application No. 12/273,670, filed on Nov. 19, 2008, now Pat. No. 8,951,286, which is a division of application No. 11/174,951, filed on Jul. 5, 2005, now Pat. No. 8,951,285.

(52) U.S. Cl.
CPC . *A61B 17/0487* (2013.01); *A61B 2017/00243* (2013.01); *A61B 2017/00783* (2013.01); *A61B 2017/0406* (2013.01); *A61B 2017/048* (2013.01); *A61B 2017/0417* (2013.01); *A61B 2017/0419* (2013.01); *A61B 2017/0458* (2013.01); *A61B 2017/0464* (2013.01); *A61B 2017/0496* (2013.01)

(56) References Cited

U.S. PATENT DOCUMENTS

| | | |
|---|---|---|
| 3,656,185 A | 4/1972 | Carpentier |
| 3,674,014 A | 7/1972 | Tillander |
| 3,794,041 A | 2/1974 | Frei et al. |
| 3,840,018 A | 10/1974 | Heifetz |
| 3,841,521 A | 10/1974 | Jarvik |
| 3,881,366 A | 5/1975 | Bradley et al. |
| 3,898,701 A | 8/1975 | La Russa |
| 3,959,960 A | 6/1976 | Santos |
| 3,986,493 A | 10/1976 | Hendren, III |
| 3,995,619 A | 12/1976 | Glatzer |
| 4,042,979 A | 8/1977 | Angell |
| 4,055,861 A | 11/1977 | Carpentier et al. |
| 4,118,805 A | 10/1978 | Reimels |
| 4,214,349 A | 7/1980 | Munch |
| 4,258,705 A | 3/1981 | Sorensen et al. |
| 4,261,342 A | 4/1981 | Aranguren Duo |
| 4,290,151 A | 9/1981 | Massana |
| 4,369,787 A | 1/1983 | Lasner et al. |
| 4,434,828 A | 3/1984 | Trincia |
| 4,473,928 A | 10/1984 | Johnson |
| 4,489,446 A | 12/1984 | Reed |
| 4,532,926 A | 8/1985 | O'Holla |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,809,713 A | 3/1989 | Grayzel |
| 4,917,698 A | 4/1990 | Carpentier et al. |
| 4,945,912 A | 8/1990 | Langberg |
| 4,961,738 A | 10/1990 | Mackin |
| 5,016,353 A | 5/1991 | Iten |
| 5,041,129 A | 8/1991 | Hayhurst et al. |
| 5,041,130 A | 8/1991 | Cosgrove et al. |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,123,914 A | 6/1992 | Cope |
| 5,171,232 A | 12/1992 | Castillo et al. |
| 5,171,259 A | 12/1992 | Inoue |
| 5,192,302 A | 3/1993 | Kensey et al. |
| 5,201,880 A | 4/1993 | Wright et al. |
| 5,203,777 A | 4/1993 | Lee |
| 5,258,008 A | 11/1993 | Wilk |
| 5,300,034 A | 4/1994 | Behnke et al. |
| 5,304,190 A | 4/1994 | Reckelhoff et al. |
| 5,306,234 A | 4/1994 | Johnson |
| 5,306,296 A | 4/1994 | Wright et al. |
| 5,325,845 A | 7/1994 | Adair |
| 5,337,736 A | 8/1994 | Reddy |
| 5,346,498 A | 9/1994 | Greelis et al. |
| 5,360,444 A | 11/1994 | Kusuhara |
| 5,364,365 A | 11/1994 | Wortrich |
| 5,364,393 A | 11/1994 | Auth et al. |
| 5,383,852 A | 1/1995 | Stevens-Wright |
| 5,429,131 A | 7/1995 | Scheinman et al. |
| 5,449,368 A | 9/1995 | Kuzmak |
| 5,450,860 A | 9/1995 | O'Connor |
| 5,452,513 A | 9/1995 | Zinnbauer et al. |
| 5,464,023 A | 11/1995 | Viera |
| 5,464,404 A | 11/1995 | Abela et al. |
| 5,474,518 A | 12/1995 | Fairer Velazquez |
| 5,477,856 A | 12/1995 | Lundquist |
| 5,545,178 A | 8/1996 | Kensey et al. |
| 5,565,122 A | 10/1996 | Zinnbauer et al. |
| 5,571,215 A | 11/1996 | Sterman et al. |
| 5,593,424 A | 1/1997 | Northrup |
| 5,601,572 A | 2/1997 | Middleman et al. |
| 5,607,471 A | 3/1997 | Seguin et al. |
| 5,623,943 A | 4/1997 | Hackett et al. |
| 5,626,590 A | 5/1997 | Wilk |
| 5,626,609 A | 5/1997 | Zvenyatsky et al. |
| 5,640,955 A | 6/1997 | Ockuly et al. |
| 5,643,317 A | 7/1997 | Pavcnik et al. |
| 5,662,681 A | 9/1997 | Nash |
| 5,669,919 A | 9/1997 | Sanders et al. |
| 5,674,279 A | 10/1997 | Wright et al. |
| 5,676,653 A | 10/1997 | Taylor et al. |
| 5,682,906 A | 11/1997 | Sterman et al. |
| 5,683,402 A | 11/1997 | Cosgrove et al. |
| 5,690,656 A | 11/1997 | Cope et al. |
| 5,702,397 A | 12/1997 | Goble |
| 5,702,398 A | 12/1997 | Tarabishy |
| 5,706,827 A | 1/1998 | Ehr et al. |
| 5,709,695 A | 1/1998 | Northrup, III |
| 5,716,367 A | 2/1998 | Koike et al. |
| 5,716,370 A | 2/1998 | Williamson, IV et al. |
| 5,716,397 A | 2/1998 | Myers |
| 5,716,399 A | 2/1998 | Love |
| 5,728,116 A | 3/1998 | Rosenman |
| 5,730,150 A | 3/1998 | Peppel et al. |
| 5,749,371 A | 5/1998 | Zadini et al. |
| 5,776,080 A | 7/1998 | Thome et al. |
| 5,776,189 A | 7/1998 | Khalid |
| 5,782,844 A | 7/1998 | Yoon et al. |
| 5,797,939 A | 8/1998 | Yaan |
| 5,810,882 A | 9/1998 | Bolduc et al. |
| 5,813,996 A | 9/1998 | St. Germain et al. |
| 5,824,066 A | 10/1998 | Gross |
| 5,827,300 A | 10/1998 | Fleega |
| 5,829,447 A | 11/1998 | Stevens et al. |
| 5,830,221 A | 11/1998 | Stein et al. |
| 5,830,224 A | 11/1998 | Cohn et al. |
| 5,843,120 A | 12/1998 | Israel et al. |
| 5,851,185 A | 12/1998 | Berns |
| 5,855,614 A | 1/1999 | Stevens et al. |
| 5,860,920 A | 1/1999 | McGee et al. |
| 5,868,733 A | 2/1999 | Ockuly et al. |
| 5,876,373 A | 3/1999 | Giba et al. |
| 5,879,366 A | 3/1999 | Shaw |
| 5,888,240 A | 3/1999 | Carpentier et al. |
| 5,906,579 A | 5/1999 | Vander Salm et al. |
| 5,911,720 A | 6/1999 | Bourne et al. |
| 5,928,224 A | 7/1999 | Laufer |
| 5,931,818 A | 8/1999 | Werp et al. |
| 5,935,098 A | 8/1999 | Blaisdell et al. |
| 5,944,738 A | 8/1999 | Amplatz et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,980,515 A | 11/1999 | Tu |
| 5,984,939 A | 11/1999 | Yaan |
| 5,984,959 A | 11/1999 | Robertson et al. |
| 6,015,414 A | 1/2000 | Werp et al. |
| 6,027,514 A | 2/2000 | Stine et al. |
| 6,042,554 A | 3/2000 | Rosenman et al. |
| 6,042,581 A | 3/2000 | Ryan et al. |
| 6,045,497 A | 4/2000 | Schweich, Jr. et al. |
| 6,050,472 A | 4/2000 | Shibata |
| 6,050,936 A | 4/2000 | Schweich, Jr. et al. |
| 6,059,715 A | 5/2000 | Schweich, Jr. et al. |
| 6,068,637 A | 5/2000 | Popov et al. |
| 6,068,648 A | 5/2000 | Cole et al. |
| 6,071,292 A | 6/2000 | Makower et al. |

(56) References Cited

U.S. PATENT DOCUMENTS

| | | |
|---|---|---|
| 6,074,341 A | 6/2000 | Anderson et al. |
| 6,074,401 A | 6/2000 | Gardiner et al. |
| 6,074,417 A | 6/2000 | Peredo |
| 6,080,182 A | 6/2000 | Shaw et al. |
| 6,086,582 A | 7/2000 | Altman et al. |
| 6,099,460 A | 8/2000 | Denker |
| 6,102,945 A | 8/2000 | Campbell |
| 6,106,550 A | 8/2000 | Magovern et al. |
| 6,110,200 A | 8/2000 | Hinnenkamp |
| 6,113,611 A | 9/2000 | Allen et al. |
| 6,126,647 A | 10/2000 | Posey et al. |
| 6,132,390 A | 10/2000 | Cookston et al. |
| RE36,974 E | 11/2000 | Bonutti |
| 6,143,024 A | 11/2000 | Campbell et al. |
| 6,159,234 A | 12/2000 | Bonutti et al. |
| 6,159,240 A | 12/2000 | Sparer et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,183 A | 12/2000 | Kuehn et al. |
| 6,173,199 B1 | 1/2001 | Gabriel |
| 6,174,332 B1 | 1/2001 | Loch et al. |
| 6,183,411 B1 | 2/2001 | Mortier et al. |
| 6,187,040 B1 | 2/2001 | Wright |
| 6,190,353 B1 | 2/2001 | Makower et al. |
| 6,197,017 B1 | 3/2001 | Brock et al. |
| 6,206,895 B1 | 3/2001 | Levinson |
| 6,210,347 B1 | 4/2001 | Forsell |
| 6,210,432 B1 | 4/2001 | Solem et al. |
| 6,217,610 B1 | 4/2001 | Carpentier et al. |
| 6,231,587 B1 | 5/2001 | Makower |
| 6,231,602 B1 | 5/2001 | Carpentier et al. |
| 6,251,092 B1 | 6/2001 | Qin et al. |
| 6,267,781 B1 | 7/2001 | Tu |
| 6,269,819 B1 | 8/2001 | Oz et al. |
| 6,285,903 B1 | 9/2001 | Rosenthal et al. |
| 6,287,317 B1 | 9/2001 | Makower et al. |
| 6,296,656 B1 | 10/2001 | Bolduc et al. |
| 6,298,257 B1 | 10/2001 | Hall et al. |
| 6,306,133 B1 | 10/2001 | Tu et al. |
| 6,312,447 B1 | 11/2001 | Grimes |
| 6,315,784 B1 | 11/2001 | Djurovic |
| 6,319,263 B1 | 11/2001 | Levinson |
| 6,319,281 B1 | 11/2001 | Patel |
| 6,328,746 B1 | 12/2001 | Gambale |
| 6,332,089 B1 | 12/2001 | Acker et al. |
| 6,332,893 B1 | 12/2001 | Mortier et al. |
| 6,352,543 B1 | 3/2002 | Cole |
| 6,355,030 B1 | 3/2002 | Aldrich et al. |
| 6,361,559 B1 | 3/2002 | Houser et al. |
| 6,368,348 B1 | 4/2002 | Gabbay |
| 6,385,472 B1 | 5/2002 | Hall et al. |
| 6,401,720 B1 | 6/2002 | Stevens et al. |
| 6,402,680 B2 | 6/2002 | Mortier et al. |
| 6,402,760 B2 | 6/2002 | Williamson, IV et al. |
| 6,402,781 B1 | 6/2002 | Langberg et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,447,522 B2 | 9/2002 | Gambale et al. |
| 6,451,054 B1 | 9/2002 | Stevens |
| 6,458,076 B1 | 10/2002 | Pruitt |
| 6,461,366 B1 | 10/2002 | Seguin |
| 6,470,892 B1 | 10/2002 | Forsell |
| 6,500,184 B1 | 12/2002 | Chan et al. |
| 6,503,274 B1 | 1/2003 | Howanec, Jr. et al. |
| 6,524,303 B1 | 2/2003 | Garibaldi |
| 6,524,338 B1 | 2/2003 | Gundry |
| 6,530,952 B2 | 3/2003 | Vesely |
| 6,533,772 B1 | 3/2003 | Sherts et al. |
| 6,537,198 B1 | 3/2003 | Vidlund et al. |
| 6,537,314 B2 | 3/2003 | Langberg et al. |
| 6,542,766 B2 | 4/2003 | Hall et al. |
| 6,544,230 B1 | 4/2003 | Flaherty et al. |
| 6,547,801 B1 | 4/2003 | Dargent et al. |
| 6,554,845 B1 | 4/2003 | Fleenor et al. |
| 6,554,852 B1 | 4/2003 | Oberlander |
| 6,562,019 B1 | 5/2003 | Sell |
| 6,564,805 B2 | 5/2003 | Garrison et al. |
| 6,565,562 B1 | 5/2003 | Shah et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,589,208 B2 | 7/2003 | Ewers et al. |
| 6,592,593 B1 | 7/2003 | Parodi et al. |
| 6,594,517 B1 | 7/2003 | Nevo |
| 6,596,014 B2 | 7/2003 | Levinson et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,919 B1 | 9/2003 | Swanstrom |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,655,386 B1 | 12/2003 | Makower et al. |
| 6,656,221 B2 | 12/2003 | Taylor et al. |
| 6,669,687 B1 | 12/2003 | Saadat |
| 6,669,707 B1 | 12/2003 | Swanstrom et al. |
| 6,676,702 B2 | 1/2004 | Mathis |
| 6,682,558 B2 | 1/2004 | Tu et al. |
| 6,689,125 B1 | 2/2004 | Keith et al. |
| 6,689,164 B1 | 2/2004 | Sequin |
| 6,695,866 B1 | 2/2004 | Kuehn et al. |
| 6,699,263 B2 | 3/2004 | Cope |
| 6,702,825 B2 | 3/2004 | Frazier et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,112 B2 | 5/2004 | Levinson |
| 6,730,121 B2 | 5/2004 | Ortiz et al. |
| 6,733,509 B2 | 5/2004 | Nobles et al. |
| 6,736,808 B1 | 5/2004 | Motamedi et al. |
| 6,746,472 B2 | 6/2004 | Frazier et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,500 B1 | 7/2004 | Muijs Van De Moer et al. |
| 6,764,510 B2 | 7/2004 | Vidlund et al. |
| 6,764,810 B2 | 7/2004 | Ma et al. |
| 6,769,434 B2 | 8/2004 | Liddicoat et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,793,618 B2 | 9/2004 | Schweich, Jr. et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,866,673 B2 | 3/2005 | Oren et al. |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,913,608 B2 | 7/2005 | Liddicoat et al. |
| 6,918,917 B1 | 7/2005 | Nguyen et al. |

(56) References Cited

U.S. PATENT DOCUMENTS

| | | |
|---|---|---|
| 6,921,407 B2 | 7/2005 | Nguyen et al. |
| 6,923,823 B1 | 8/2005 | Bartlett et al. |
| 6,926,730 B1 | 8/2005 | Nguyen et al. |
| 6,942,694 B2 | 9/2005 | Liddicoat et al. |
| 6,945,978 B1 | 9/2005 | Hyde |
| 6,960,217 B2 | 11/2005 | Bolduc |
| 6,964,683 B2 | 11/2005 | Kowalsky et al. |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,004,958 B2 | 2/2006 | Adams et al. |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,115,110 B2 | 10/2006 | Frazier et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,211,094 B2 | 5/2007 | Gannoe et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,247,134 B2 | 7/2007 | Vidlund et al. |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,731,732 B2 | 6/2010 | Ken |
| 7,736,388 B2 | 6/2010 | Goldfarb et al. |
| 7,748,389 B2 | 7/2010 | Salahieh et al. |
| 7,749,250 B2 | 7/2010 | Stone et al. |
| 7,753,924 B2 | 7/2010 | Starksen et al. |
| 7,758,632 B2 | 7/2010 | Hojeibane et al. |
| 7,771,455 B2 | 8/2010 | Ken |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,931,580 B2 | 4/2011 | Gertner et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,172,871 B2 | 5/2012 | Ken |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |

(56) References Cited

U.S. PATENT DOCUMENTS

| | | | |
|---|---|---|---|
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,689,861 B2 | 11/2014 | Skead et al. |
| 8,888,843 B2 | 11/2014 | Khairkhahan et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 * | 2/2015 | Sugimoto ........ A61B 17/00234 606/232 |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,814,454 B2 * | 11/2017 | Sugimoto ........ A61B 17/00234 |
| 9,907,547 B2 | 3/2018 | Gilmore et al. |
| 10,368,852 B2 | 8/2019 | Gerhardt et al. |
| 2001/0005787 A1 | 6/2001 | Oz et al. |
| 2001/0021874 A1 | 9/2001 | Carpentier et al. |
| 2001/0039436 A1 | 11/2001 | Frazier et al. |
| 2001/0049492 A1 | 12/2001 | Frazier et al. |
| 2001/0051815 A1 | 12/2001 | Esplin |
| 2002/0013571 A1 | 1/2002 | Goldfarb et al. |
| 2002/0016628 A1 | 2/2002 | Langberg et al. |
| 2002/0019649 A1 | 2/2002 | Sikora et al. |
| 2002/0022862 A1 | 2/2002 | Grafton et al. |
| 2002/0026198 A1 | 2/2002 | Ockuly et al. |
| 2002/0026216 A1 | 2/2002 | Grimes |
| 2002/0029080 A1 | 3/2002 | Mortier et al. |
| 2002/0042621 A1 | 4/2002 | Liddicoat et al. |
| 2002/0072758 A1 | 6/2002 | Reo et al. |
| 2002/0082525 A1 | 6/2002 | Oslund et al. |
| 2002/0087048 A1 | 7/2002 | Brock et al. |
| 2002/0087169 A1 | 7/2002 | Brock et al. |
| 2002/0087173 A1 | 7/2002 | Alferness et al. |
| 2002/0087178 A1 | 7/2002 | Nobles et al. |
| 2002/0095167 A1 | 7/2002 | Liddicoat et al. |
| 2002/0100485 A1 | 8/2002 | Stevens et al. |
| 2002/0103532 A1 | 8/2002 | Langberg et al. |
| 2002/0107531 A1 | 8/2002 | Schreck et al. |
| 2002/0128708 A1 | 9/2002 | Northrup, III et al. |
| 2002/0151916 A1 | 10/2002 | Muramatsu et al. |
| 2002/0151970 A1 | 10/2002 | Garrison et al. |
| 2002/0156526 A1 | 10/2002 | Hlavka et al. |
| 2002/0165535 A1 | 11/2002 | Lesh et al. |
| 2002/0169358 A1 | 11/2002 | Mortier et al. |
| 2002/0169359 A1 | 11/2002 | McCarthy et al. |
| 2002/0169502 A1 | 11/2002 | Mathis |
| 2002/0169504 A1 | 11/2002 | Alferness et al. |
| 2002/0173841 A1 | 11/2002 | Ortiz et al. |
| 2002/0177904 A1 | 11/2002 | Huxel et al. |
| 2002/0183766 A1 | 12/2002 | Sequin |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0018358 A1 | 1/2003 | Saadat |
| 2003/0050693 A1 | 3/2003 | Quijano et al. |
| 2003/0069593 A1 | 4/2003 | Tremulis et al. |
| 2003/0069636 A1 | 4/2003 | Solem et al. |
| 2003/0078465 A1 | 4/2003 | Pai et al. |
| 2003/0078653 A1 | 4/2003 | Vesely et al. |
| 2003/0078654 A1 | 4/2003 | Taylor et al. |

(56) References Cited

U.S. PATENT DOCUMENTS

| | | |
|---|---|---|
| 2003/0078671 A1 | 4/2003 | Lesniak et al. |
| 2003/0083538 A1 | 5/2003 | Adams et al. |
| 2003/0105474 A1 | 6/2003 | Bonutti |
| 2003/0105519 A1 | 6/2003 | Fasol et al. |
| 2003/0105520 A1 | 6/2003 | Alferness et al. |
| 2003/0114901 A1 | 6/2003 | Loeb et al. |
| 2003/0120340 A1 | 6/2003 | Liska et al. |
| 2003/0130730 A1 | 7/2003 | Cohn et al. |
| 2003/0144657 A1 | 7/2003 | Bowe et al. |
| 2003/0144697 A1 | 7/2003 | Mathis et al. |
| 2003/0160721 A1 | 8/2003 | Gilboa et al. |
| 2003/0171760 A1 | 9/2003 | Gambale |
| 2003/0171776 A1 | 9/2003 | Adams et al. |
| 2003/0171806 A1 | 9/2003 | Mathis et al. |
| 2003/0199974 A1 | 10/2003 | Lee et al. |
| 2003/0204195 A1 | 10/2003 | Keane et al. |
| 2003/0204205 A1 | 10/2003 | Sauer et al. |
| 2003/0208195 A1 | 11/2003 | Thompson et al. |
| 2003/0212453 A1 | 11/2003 | Mathis et al. |
| 2003/0220685 A1 | 11/2003 | Hlavka et al. |
| 2003/0229350 A1 | 12/2003 | Kay |
| 2003/0229395 A1 | 12/2003 | Cox |
| 2003/0233142 A1 | 12/2003 | Morales et al. |
| 2004/0003819 A1 | 1/2004 | St. Goar et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0024451 A1 | 2/2004 | Johnson et al. |
| 2004/0030382 A1 | 2/2004 | Sl. Goar et al. |
| 2004/0039442 A1 | 2/2004 | Sl. Goar et al. |
| 2004/0044364 A1 | 3/2004 | DeVries et al. |
| 2004/0049211 A1 | 3/2004 | Tremulis et al. |
| 2004/0059413 A1 | 3/2004 | Argento |
| 2004/0092962 A1 | 5/2004 | Thornton et al. |
| 2004/0093023 A1 | 5/2004 | Allen et al. |
| 2004/0097865 A1 | 5/2004 | Anderson et al. |
| 2004/0122456 A1 | 6/2004 | Saadat et al. |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133063 A1 | 7/2004 | McCarthy et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0147958 A1 | 7/2004 | Lam et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0152947 A1 | 8/2004 | Schroeder et al. |
| 2004/0162568 A1 | 8/2004 | Saadat et al. |
| 2004/0167539 A1 | 8/2004 | Kuehn et al. |
| 2004/0167620 A1 | 8/2004 | Ortiz et al. |
| 2004/0172046 A1 | 9/2004 | Hlavka et al. |
| 2004/0176788 A1 | 9/2004 | Opolski |
| 2004/0181287 A1 | 9/2004 | Gellman |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0220473 A1 | 11/2004 | Lualdi |
| 2004/0236419 A1 | 11/2004 | Milo |
| 2004/0243153 A1 | 12/2004 | Liddicoat et al. |
| 2004/0243227 A1 | 12/2004 | Starksen et al. |
| 2004/0260317 A1 | 12/2004 | Bloom et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0033446 A1 | 2/2005 | Deem et al. |
| 2005/0049634 A1 | 3/2005 | Chopra |
| 2005/0049681 A1 | 3/2005 | Greenhalgh et al. |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0055089 A1 | 3/2005 | Macoviak et al. |
| 2005/0060030 A1 | 3/2005 | Lashinski et al. |
| 2005/0065550 A1 | 3/2005 | Starksen et al. |
| 2005/0065601 A1 | 3/2005 | Lee et al. |
| 2005/0070999 A1 | 3/2005 | Spence |
| 2005/0075723 A1 | 4/2005 | Schroeder et al. |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107810 A1 | 5/2005 | Morales et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119734 A1 | 6/2005 | Spence et al. |
| 2005/0119735 A1 | 6/2005 | Spence et al. |
| 2005/0125002 A1 | 6/2005 | Baran et al. |
| 2005/0125011 A1 | 6/2005 | Spence et al. |
| 2005/0125031 A1 | 6/2005 | Pupenhagen et al. |
| 2005/0131438 A1 | 6/2005 | Cohn |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137700 A1 | 6/2005 | Spence et al. |
| 2005/0143811 A1 | 6/2005 | Realyvasquez |
| 2005/0148815 A1 | 7/2005 | Mortier et al. |
| 2005/0149014 A1 | 7/2005 | Hauck et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0184122 A1 | 8/2005 | Hlavka et al. |
| 2005/0187568 A1 | 8/2005 | Klenk et al. |
| 2005/0192596 A1 | 9/2005 | Jugenheimer |
| 2005/0197693 A1 | 9/2005 | Pai et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0251157 A1 | 11/2005 | Saadat et al. |
| 2005/0251159 A1 | 11/2005 | Ewers et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0256532 A1 | 11/2005 | Nayak et al. |
| 2005/0267478 A1 | 12/2005 | Corradi et al. |
| 2005/0267533 A1 | 12/2005 | Gertner |
| 2005/0267571 A1 | 12/2005 | Spence et al. |
| 2005/0273138 A1 | 12/2005 | To et al. |
| 2005/0283192 A1 | 12/2005 | Torrie et al. |
| 2005/0288694 A1 | 12/2005 | Solomon |
| 2005/0288778 A1 | 12/2005 | Shaoulian et al. |
| 2006/0004410 A1 | 1/2006 | Nobis et al. |
| 2006/0004442 A1 | 1/2006 | Spenser et al. |
| 2006/0004443 A1 | 1/2006 | Liddicoat et al. |
| 2006/0009784 A1 | 1/2006 | Behl et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |

(56) References Cited

U.S. PATENT DOCUMENTS

| | | |
|---|---|---|
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142756 A1 | 6/2006 | Davies et al. |
| 2006/0149280 A1 | 7/2006 | Harvie et al. |
| 2006/0149368 A1 | 7/2006 | Spence |
| 2006/0161040 A1 | 7/2006 | McCarthy et al. |
| 2006/0161265 A1 | 7/2006 | Levine et al. |
| 2006/0178682 A1 | 8/2006 | Boehlke |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0212045 A1 | 9/2006 | Schilling et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010857 A1 | 1/2007 | Sugimoto et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0038221 A1 | 2/2007 | Fine |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0055303 A1 | 3/2007 | Vidlund et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106310 A1 | 5/2007 | Goldin et al. |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112424 A1 | 5/2007 | Spence et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228165 A1 | 9/2008 | Spence et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275503 A1 | 11/2008 | Spence et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0018655 A1 | 1/2009 | Brunelle et al. |
| 2009/0028670 A1 | 1/2009 | Garcia et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249908 A1 | 9/2010 | Chau et al. |

(56) References Cited

U.S. PATENT DOCUMENTS

| | | |
|---|---|---|
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2014/0081394 A1 | 3/2014 | Keranen et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0112432 A1 | 4/2015 | Reich et al. |
| 2015/0127097 A1 | 5/2015 | Neumann et al. |
| 2015/0182336 A1 | 7/2015 | Zipory et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0224489 A1 | 8/2017 | Starksen et al. |
| 2017/0245993 A1 | 8/2017 | Gross et al. |
| 2018/0049875 A1 | 2/2018 | Iflah et al. |
| 2018/0318080 A1 | 11/2018 | Quill et al. |
| 2019/0038411 A1 | 2/2019 | Alon |

FOREIGN PATENT DOCUMENTS

| | | |
|---|---|---|
| EP | 2181670 | 5/2010 |
| EP | 3531975 A1 | 9/2019 |
| WO | 9205093 A1 | 4/1992 |
| WO | WO 9604852 | 2/1996 |
| WO | 9846149 A1 | 10/1998 |
| WO | WO 9900059 | 1/1999 |
| WO | WO 0003759 | 1/2000 |
| WO | WO 0044311 | 8/2000 |
| WO | WO 0060995 | 10/2000 |
| WO | WO 0067640 | 11/2000 |
| WO | WO 0200099 | 1/2002 |
| WO | WO 02051329 | 7/2002 |
| WO | WO 02096275 | 12/2002 |
| WO | WO 03001893 | 1/2003 |
| WO | WO 03007796 | 1/2003 |
| WO | 02085250 A3 | 2/2003 |
| WO | 03047467 A1 | 6/2003 |
| WO | WO 03053289 | 7/2003 |
| WO | WO 03/077772 | 9/2003 |
| WO | WO 2004/037317 | 5/2004 |
| WO | WO 2004045378 | 6/2004 |
| WO | WO 2004/112658 | 12/2004 |
| WO | WO 2005011463 | 2/2005 |

(56) References Cited

FOREIGN PATENT DOCUMENTS

| WO | WO 2005013832 | 2/2005 |
|---|---|---|
| WO | WO 2005025644 | 3/2005 |
| WO | WO 200558239 | 6/2005 |
| WO | WO 2006/039296 | 4/2006 |
| WO | WO 06064490 | 6/2006 |
| WO | WO 2006105008 | 10/2006 |
| WO | WO 07005394 | 1/2007 |
| WO | WO 200891391 | 7/2008 |
| WO | 2010000454 A1 | 1/2010 |
| WO | 2012176195 A3 | 3/2013 |
| WO | 2014064964 A1 | 5/2014 |

OTHER PUBLICATIONS

F. Maisano et al., The Double-Orifice Technique as a Standardized Approach to Treat Mitral Regurgitation Due to Severe Myxomatous Disease: Surgical Technique, European Journal of Cardio-thoracis Surgery, 1998.
Douglas P. Zipes, MD et al., Ablation of Free Wall Accessory Pathways, Catheter Ablation of Arrhythmias, Chapter 8, 7 pgs., 1994.
David L.S. Morales et al., Development of an Off Bypass Mitral Valve Repair, Department of Surgery, Columbia University, College of Physicians and Surgeons, New York, NY. Apr. 13, 1999.
Heart Surgery Forum, Aug. 8, 2000. p. 1. Tables 1-2. Web. http://www.hsforum.com/vol2/issue2/1999-4963_tables.html>.
Heart Surgery Forum, Aug. 8, 2000. pp. 1-4. Figures 1-8. Web. http://www.hsforum.comlvol2/issue2/1999-4963figures.html>.
"Heart Valves: The Duran Flexible Annuloplasty Band—For Surgeons "Partial" to Flexiblity." Medtronic. Feb. 23, 2001. Web. http://medtronic.com/cardiac/heartvalves/duran_band/>.
Zsolt L. Nagy et al., Mitral Annuloplasty With a Suture Technique, European Journal of Cardio-thoracic Surgery 18. Aug. 15, 2000, 1 pg.
Agarwal et al. International Cardiology Perspective Functional Tricuspid Regurgitation, Circ Cardiovasc Interv 2009;2;2;565-573 (2009).
Ahmadi, A., G. Spillner, and Th Johannesson, "Hemodynamic changes following experimental production and correction of acute mitral regurgitation with an adjustable ring prosthesis." The Thoracic and cardiovascular surgeon36.06 (1988): 313-319.
Ahmadi, All et al. "Percutaneously adjustable pulmonary artery band." The Annals of thoracic surgery 60 (1995): S520-S522.
Alfieri et al."Novel Suture Device for Beating-Heart Mitral Leaflet Approximation", Ann Thorac Surg. 2002, 74:1488-1493.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. Ring+String, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
O'Reilly S et al., "Heart valve surgery pushes the envelope," Medtech Insight 8(3): 73, 99-108 (2006).
Odell JA et al., "Early Results o4yf a Simplified Method of Mitral Valve Annuloplasty," Circulation 92:150-154 (1995).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

\* cited by examiner

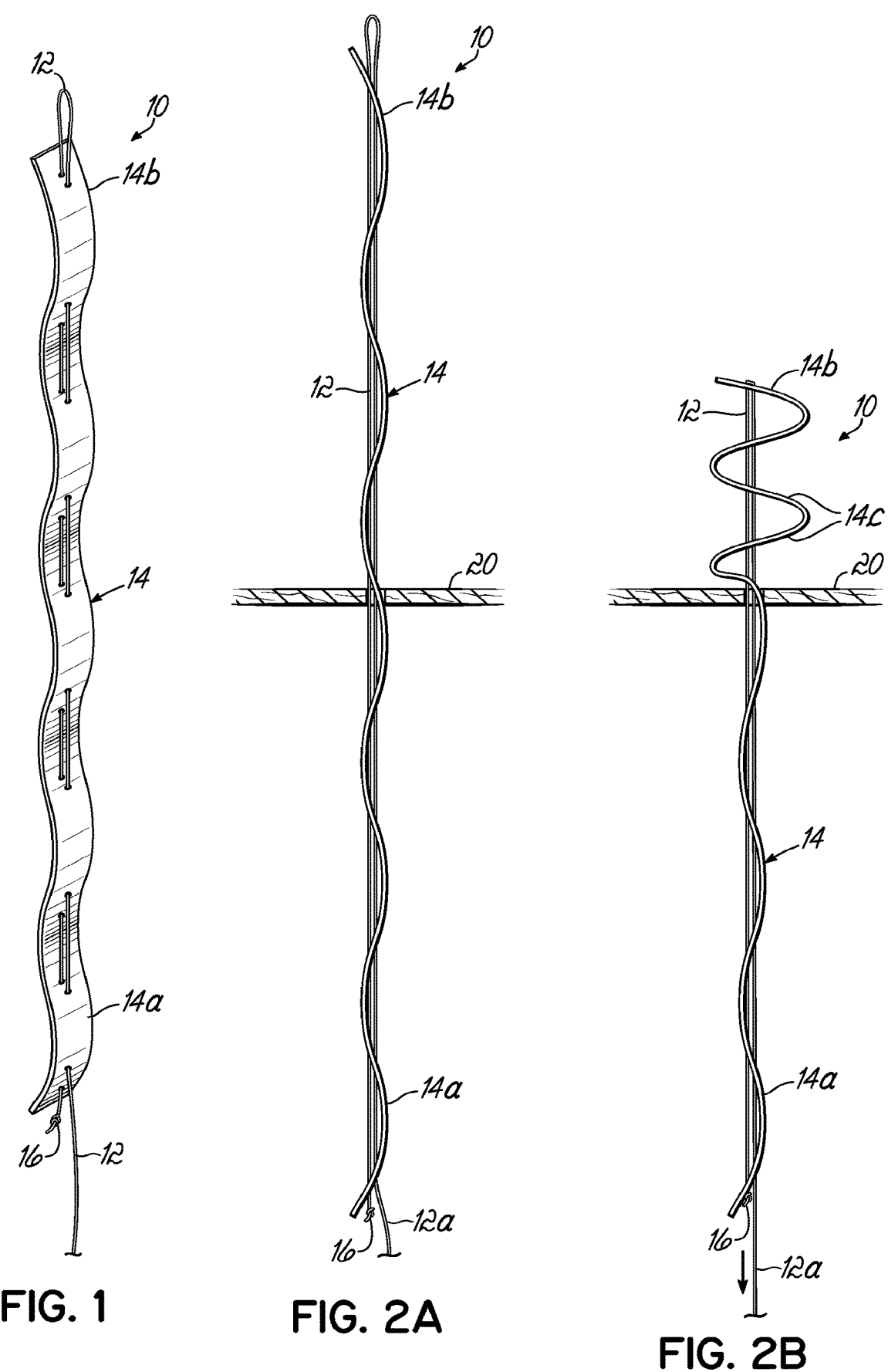

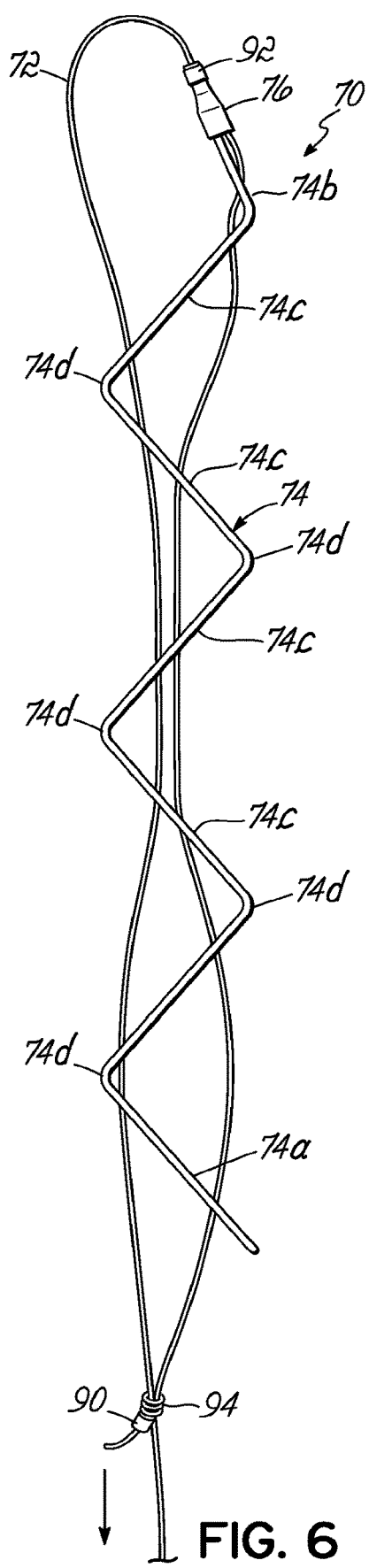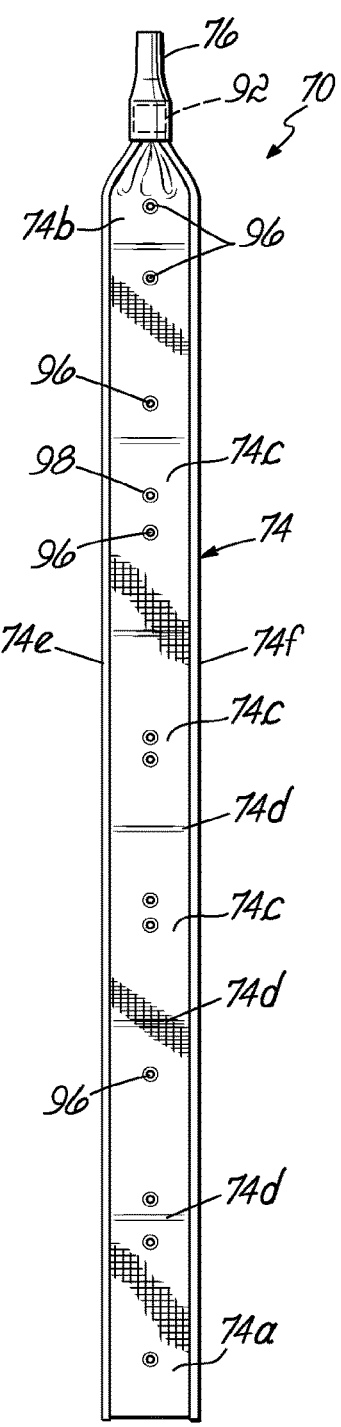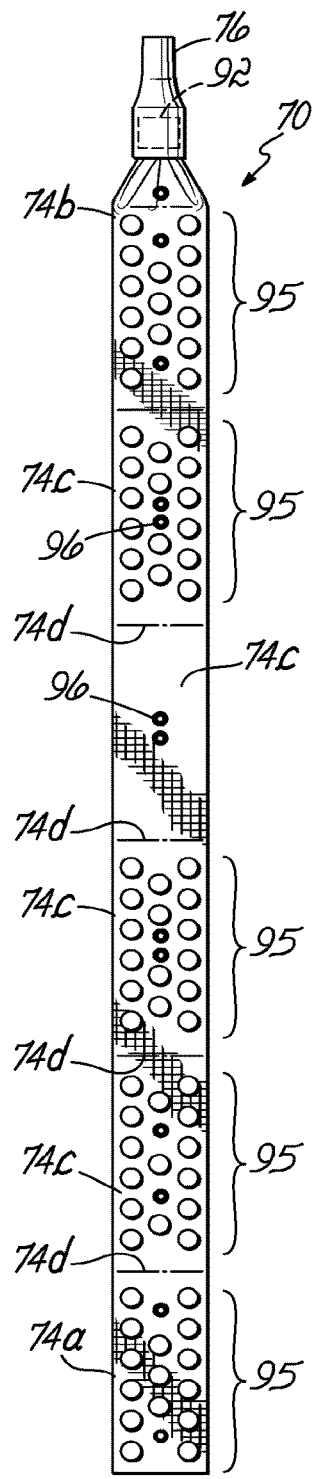
FIG. 6
FIG. 7
FIG. 7A

TISSUE ANCHOR AND ANCHORING SYSTEM

CROSS-REFERENCE TO RELATED APPLICATIONS

This application is a continuation of U.S. patent application Ser. No. 14/581,264, filed Dec. 23, 2014, which is a continuation of U.S. patent application Ser. No. 12/273,670, filed Nov. 19, 2008, which is a divisional of U.S. patent application Ser. No. 11/174,951, filed Jul. 5, 2005, now U.S. Pat. No. 8,951,285, issued Feb. 10, 2015, the contents of each of which are incorporated by reference in their entireties.

TECHNICAL FIELD

The present invention generally relates to tissue anchors and, more particularly, anchors and methods of using such anchors to secure an element or otherwise provide an anchor point to biological tissue and/or to secure at least two tissue portions together.

BACKGROUND

Many different surgical procedures require that an anchor be used to either establish a strong point of connection for other securing elements or devices relative to a tissue location in a patient, and/or to secure two or more tissue layers (i.e., portions together. In this regard, the term "anchor", as used herein, is not to be limited to any particular type of tissue fastening or securement application but, rather, encompasses any hard and/or soft tissue-to-tissue securement, tissue-to-device securement, or any other tissue securement application.

One particular area that has received attention in recent years is that of catheter-based surgical procedures. Various tissue anchors have been developed for purposes of deployment and securement with catheter-based technology. However, there are still limitations in current technology. For example, insertion size versus deployment size must be strictly controlled due to the need for catheter diameters to be maintained relatively small. Many catheter-based tissue anchor systems have very specialized uses and are not versatile for use in many different tissue fastening or securement operations.

There is generally a need for a simpler, more versatile tissue anchor which may be deployed and securely fastened to tissue in a catheter-based operation or a non-catheter-based operation.

SUMMARY

In one aspect, the invention provides a tissue anchor comprising a generally flexible anchor member capable of being inserted through tissue and moving between an elongate configuration and a shortened configuration suitable for anchoring against at least one side of the tissue. The anchor member includes a proximal end portion, a distal end portion, and a compressible intermediate portion between the proximal end portion and the distal end portion. A tensioning member is operatively connected to the anchor member such that the anchor member can slide relative to the tensioning member. The tensioning member may be pulled to cause the anchor member to move relative to the tensioning member from the elongate configuration to the shortened configuration. In the shortened configuration, the compressible intermediate portion of the anchor member can compress or shorten and thereby adjust to the thickness of the tissue between the proximal and distal end portions.

In another aspect of the invention, a tissue anchor is provided comprising a flat, generally flexible anchor member capable of movement between an elongate configuration suitable for deployment and a shortened configuration suitable for anchoring against tissue. A tensioning member is operatively connected to the anchor member such that the anchor member can slide relative to the tensioning member. The tensioning member is capable of being pulled to cause the anchor member to move relative to the tensioning member from the elongate configuration to the shortened configuration.

In a further aspect of the invention, a tissue anchor is provided comprising a flat anchor member formed from a strip of fabric material and capable of movement between an elongate configuration suitable for deployment and a shortened configuration suitable for anchoring against tissue. A tensioning member is operatively connected to the anchor member such that the anchor member can slide relative to the tensioning member. The tensioning member is capable of being pulled to cause the anchor member to move relative to the tensioning member from the elongate configuration to the shortened configuration. A lock member is provided for securing the anchor member in the shortened configuration.

In a further aspect of the invention, a tissue anchor is provided comprising a flat, generally flexible anchor member capable of being inserted through tissue and moving between an elongate configuration suitable for deployment through a catheter and a shortened configuration suitable for anchoring against the tissue. A tensioning member is operatively connected to the anchor member such that the anchor member may slide relative to the tensioning member. The tensioning member is capable of being pulled to cause the anchor member to move relative to the tensioning member from the elongate configuration to the shortened configuration against the tissue.

In another aspect of the invention, a tissue anchor is provided comprising a flat elongate strip formed from a generally flexible material and having proximal and distal end portions. A tensioning member having first and second ends is operatively connected to the elongate strip such that pulling on the first end of the tensioning member causes the proximal and distal end portions of the elongate strip to move toward each other to a shortened configuration suitable for anchoring against the tissue.

In certain aspects, the anchor member is advantageously formed as a flat, generally flexible strip of material, while in other aspects it need not be a flat strip but may have other shapes, such as tubular, that may or may not be capable of assuming a flat shape. Various optional features may be incorporated into any or all of the various embodiments of the tissue anchor. For example, the tissue anchor may be formed from a material selected from at least one of: natural fibers, synthetic fibers, polymers, and metals. Such materials may be absorbable or nonabsorbable, and may be radiopaque or at least partially radiopaque. The tensioning member may further comprise a suture, or any other suitable flexible, semi-rigid or rigid tensioning member. The tensioning member may include a stop member engaged with the anchor member, such as a knot in the tensioning member, or a separate stop member (e.g., a crimp) engageable with the anchor member. The tensioning member may, for example, extend through the anchor member at multiple locations between the proximal end portion and the distal end portion. Such coupling of the tensioning member and the anchor member may be configured in many different manners depending, for example, on the desired configuration of the anchor member upon pulling the tensioning member and moving the anchor member into the shortened configuration. In one embodiment, at least one fold is formed upon pulling the tensioning member. Multiple folds may be formed in a generally zig-zag or accordion fashion. A lock member may be provided and engageable with the tensioning member to retain the anchor member in the shortened configuration. The tissue anchor may include at least one radiopaque marker on one or both of the anchor member and the tensioning member. For example, a first radiopaque marker may be located near the proximal end portion when the anchor member is in the shortened configuration and a second radiopaque marker may be located near the distal end portion when the anchor member is in the shortened configuration. The distal end portion of the anchor member may include a relatively more rigid tip as compared to the anchor member and having a reduced width as compared to an adjacent portion of the anchor member. The anchor member itself may be designed in any of numerous manners, including designs that have a uniform width along the length thereof, and designs that have a varying width along the length. Other features may be incorporated such as edge portions that are slightly more rigid than a central area of the anchor member. Entire sections of the anchor member may be relatively rigid as compared to fold line portions thereof while still resulting in a generally flexible anchor member. As necessary, hinge portions, such as living hinges, may be designed into the anchor member to allow for folding or other shortening action of the anchor member. While a tensioning member is specifically disclosed herein for activation purposes (that is, activating the anchor member from the elongate configuration to the shortened configuration), the invention in various combinations may utilize other types of activation, such as compressive activation.

Each of the embodiments of the tissue anchor may be part of a catheter-based anchoring system having a delivery catheter and a suitable deploying device associated with the delivery catheter and operable to extend the anchor member from the delivery catheter. The deploying device may further comprise a deploying catheter at least partially containing the anchor member and at least partially contained within the delivery catheter.

The invention further provides for various methods of anchoring tissue as generally described herein. For example, in one aspect a method of anchoring tissue is provided comprising inserting a generally flexible elongate anchor member through the tissue, and pulling a first end of a tensioning member coupled for sliding movement relative to the first anchor member to draw the proximal and distal end portions toward each other and to compress the intermediate portion into the shortened configuration with at least one of the proximal and distal end portions engaged against the tissue.

In another aspect of the invention, a method of tissue anchoring is provided comprising inserting the generally flexible flat elongate strip having proximal and distal end portions through the tissue, and pulling a first end of a tensioning member operatively connected to the strip to draw the proximal and distal end portions of the strip toward each other into the shortened configuration engaged against the tissue.

In another aspect, a method of tissue anchoring is provided comprising inserting the generally flexible flat elongate strip having proximal and distal end portions through the tissue, and pulling a first end of a tensioning member operatively connected to the strip to configure at least a portion of the strip into a shortened configuration engaged against the tissue.

In each of the embodiments engagement of the anchor member against the tissue may be engagement against opposite sides of at least one tissue layer, or engagement against only one side of at least one tissue layer.

Additional features and advantages of the invention will become readily apparent to those of ordinary skill in the art upon review of the following detailed description of the illustrative embodiments taken in conjunction with the accompanying illustrative figures.

BRIEF DESCRIPTION OF THE DRAWINGS

FIG. 1 is a perspective view of a tissue anchor constructed in accordance with a first embodiment of the invention.

FIG. 2A is a side view of the tissue anchor shown in FIG. 1, with the tissue anchor deployed through a layer of tissue.

FIG. 2B is a side view similar to FIG. 2A, but illustrating the distal portion of the tissue anchor being moved toward the layer of tissue.

FIG. 6 is a side elevational view illustrating the tissue anchor constructed in accordance with the second embodiment.

FIG. 7 is a front view of the elongate strip portion of the anchor.

FIG. 7A is a front elevational view similar to FIG. 7, but illustrating one embodiment of radiopaque markers used on the elongate strip.

DETAILED DESCRIPTION OF ILLUSTRATIVE EMBODIMENTS

Figure 2C:
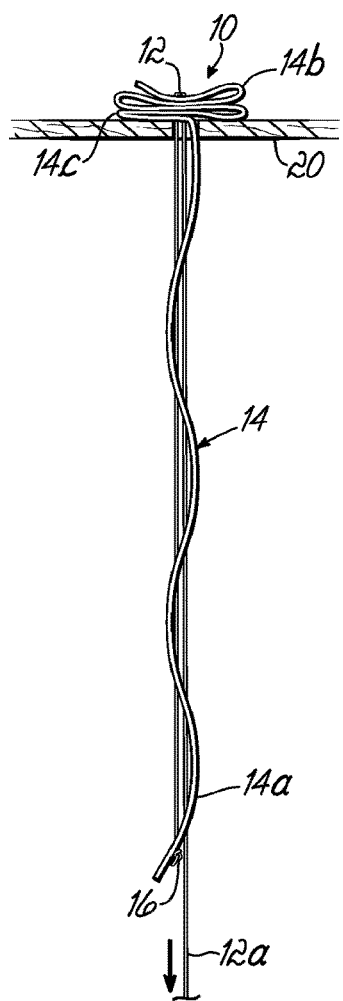
FIG. 2C is a side view similar to FIG. 2B, but showing the distal portion fully compressed and engaged against the layer of tissue.

Referring first to FIG. 1, a tissue anchor 10 constructed in accordance with a first embodiment of the invention generally includes a tensioning member 12, such as a suture, extending through spaced apart points along a flat elongate strip 14 of flexible material, such as a surgical grade fabric. It will be appreciated that the tensioning member 12 may take other forms other than suture material, such as cable or any other small diameter member having a high enough tensile strength for the intended anchoring use. The elongate strip 14 may also take various forms such as woven or nonwoven fabrics, polymers, metals or other suitable materials or combinations of materials. One or more separate pledgets or other securement members (not shown) may be used in conjunction with the elongate strip 14 for added securement and/or concealing the elongate strip 14 and, for example, thereby inhibiting blood clotting within or adjacent to the folds that will be formed in the strip 14.

A woven or nonwoven material may contain additional materials, such as threads, beads or other elements that cause at least portions of the strip 14 to be radiopaque. Currently, a surgical grade fabric constructed from polyester, such as Dacron®, is contemplated for use in constructing the strip 14. One of many possible alternative materials for use in constructing strip 14 is polytetrafluoroethylene (PTFE). Tissue anchor 10 may be partly or wholly formed from materials that are absorbed into the patient's tissue over time, depending on the intended use. The edges and/or other portions of the strip 14 may be suitably modified to prevent fraying, such as by being coated with a material that locks the fibers in place, or otherwise modified in a manner that locks the fibers at least at the edges of the strip 14 in place.

The suture 12 may extend from a proximal end portion 14a of the fabric strip 14 to a distal end portion 14b and then loop back through spaced apart points of the fabric strip 14 to the proximal end portion 14a where a knot 16 or other stop member is located for reasons to be described below. As will become apparent, the suture 12 extends through spaced apart locations along the elongate strip 14 such that tensioning of the suture 12 or other tensioning member will cause the elongate strip 14 to form folded portions 14c when the tensioning member 12 is placed under tension or pulled. Thus, the elongate strip 14 is activated in this manner between essentially an elongate deployment orientation or configuration, such as shown in FIG. 1, and a shortened configuration, such as a folded or otherwise shortened configuration having an expanded width in at least one dimension as compared to the elongate deployment configuration. It will be appreciated that the deployment orientation may take on various forms due to the flexible nature of the strip 14, especially when using a highly flexible fabric or other material. For example, a fabric material or other similarly flexible materials may be folded or otherwise deformed for carrying purposes within a catheter and/or during deployment to a tissue site and then suitably activated at the tissue site.

Figure 2D:
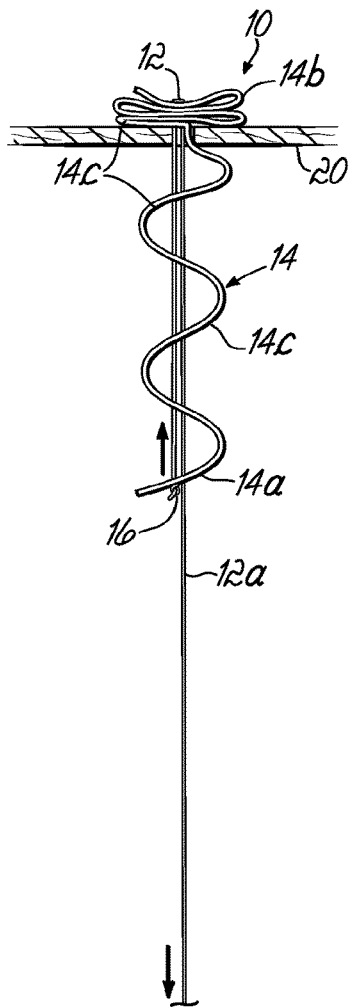
FIG. 2D is a side view similar to FIG. 2C but illustrating the proximal portion of the tissue anchor being moved toward the layer of tissue.
Figure 2E:
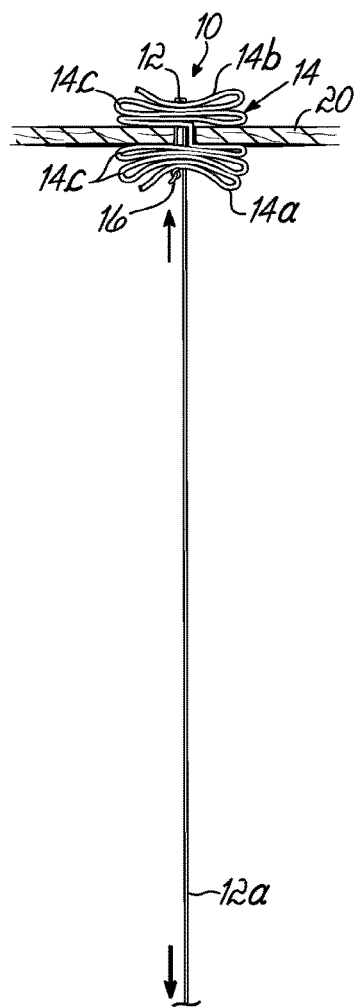
FIG. 2E illustrates the proximal and distal portions of the tissue anchor fully compressed against opposite sides of the layer of tissue.
Figure 2F:
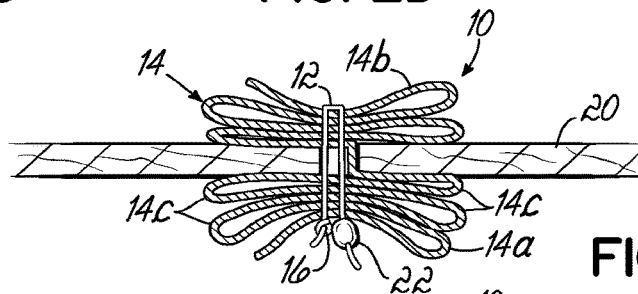
FIG. 2F is an enlarged cross sectional view illustrating the fully deployed and fastened anchor with a layer of tissue between proximal and distal anchor portions.

More specifically referring to FIGS. 2A-2E, the elongate strip 14 and attached suture 12 are initially inserted through at least one tissue layer 20 as generally shown in FIG. 2A. One end or portion 12a of the suture 12 is then pulled and thereby placed under tension. It will be appreciated that, for catheter-based procedures, suture portion 12a may extend to a location outside the patient's body for pulling or tensioning, or it may be grasped by a suitable mechanism within the catheter and pulled or tensioned. Pulling suture portion 12a may initially draw the distal portion 14b of the elongate strip 14 toward the layer of tissue 20 as shown in FIG. 2B. Once the distal portion 14b is compressed against the layer of tissue 20, the proximal portion 14a begins to be drawn and compressed against a proximal side of the tissue 20 as shown in FIGS. 2C-2E. This occurs because end 12a of the suture 12 is being pulled downwardly (as viewed for purposes of discussion in FIGS. 2C-2E) and, since the suture 12 is looped in a reverse direction through distal end portion 14b of the elongate strip 14, the knot 16 at the end of the suture 12 moves upwardly and brings the proximal portion 14a of the elongate strip 14 with it. In this manner, the proximal portion 14a of the elongate strip 14 is being folded and drawn along the suture 12 toward the layer of tissue 20 and then firmly compressed against the proximal side of the layer of tissue 20 as shown in FIG. 2E. As further shown in FIG. 2F, a suitable locker element, such as a crimp member 22, a knot or other element may be used to maintain the suture 12 and elongate strip 14 in the positions shown in FIG. 2F securely anchoring the proximal and distal portions 14a, 14b of the elongate strip 14 folded against opposite sides of the tissue 20.

Figure 3:
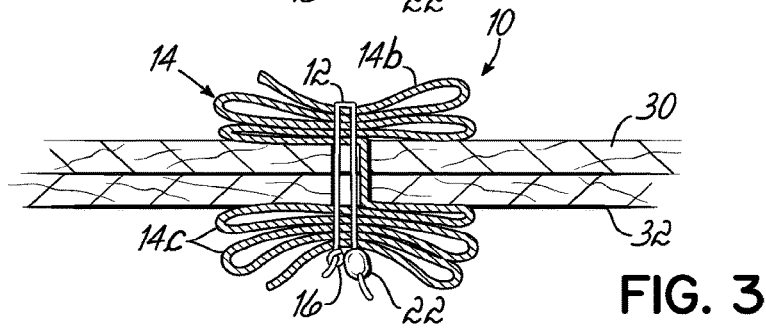
FIG. 3 is a side cross sectional view similar to FIG. 2F, but illustrating the fastening of two layers of tissue between the proximal and distal anchor portions.

As further shown in FIG. 3, the same general procedure may be used to secure two distinct tissue layers 30, 32 together by initialing extending the elongate strip 14 and tensioning member 12 through at least two layers of tissue 30, 32. In this manner, for example, two layers of tissue 30, 32 may be securely fastened together. This may, for example, involve two entirely different layers and even types of tissue or the same layer of tissue which has been folded over to effectively form two layers (i.e., portions) of tissue.

FIGS. 4A-4E schematically illustrate an annuloplasty procedure performed on a mitral valve 40 of a heart 42 utilizing tissue anchors 10 as described above in regard to the first embodiment. Performance of the annuloplasty procedure may have many variations, but is generally illustrated by the placement of at least two tissue anchors 10 and securement of the two anchors 10 together, such as with one or more tensioning members 12 therebetween. For an additional illustrative description of catheter-based annuloplasty procedures that may utilize any of the tissue anchors within the scope of the present invention, reference may be made to U.S. patent application Ser. No. 10/948,922, filed on Sep. 24, 2004, assigned to the assignee of the present invention, and the disclosure of which is hereby entirely incorporated by reference herein.

Figure 4A:
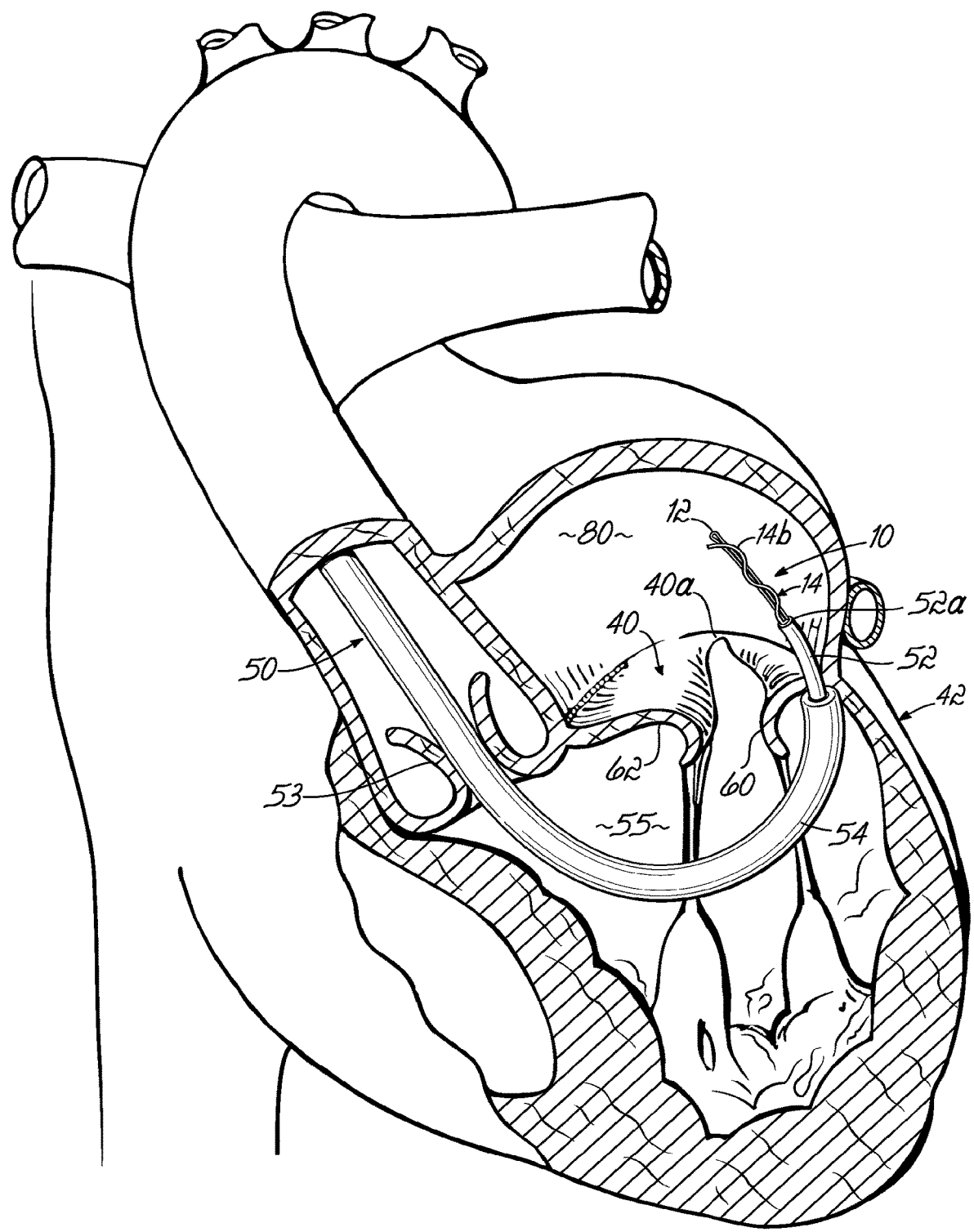
FIGS. 4A-4F are perspective views illustrating successive steps in an annuloplasty procedure on the mitral valve of a patient utilizing tissue anchors of the first embodiment.
Figure 4B:
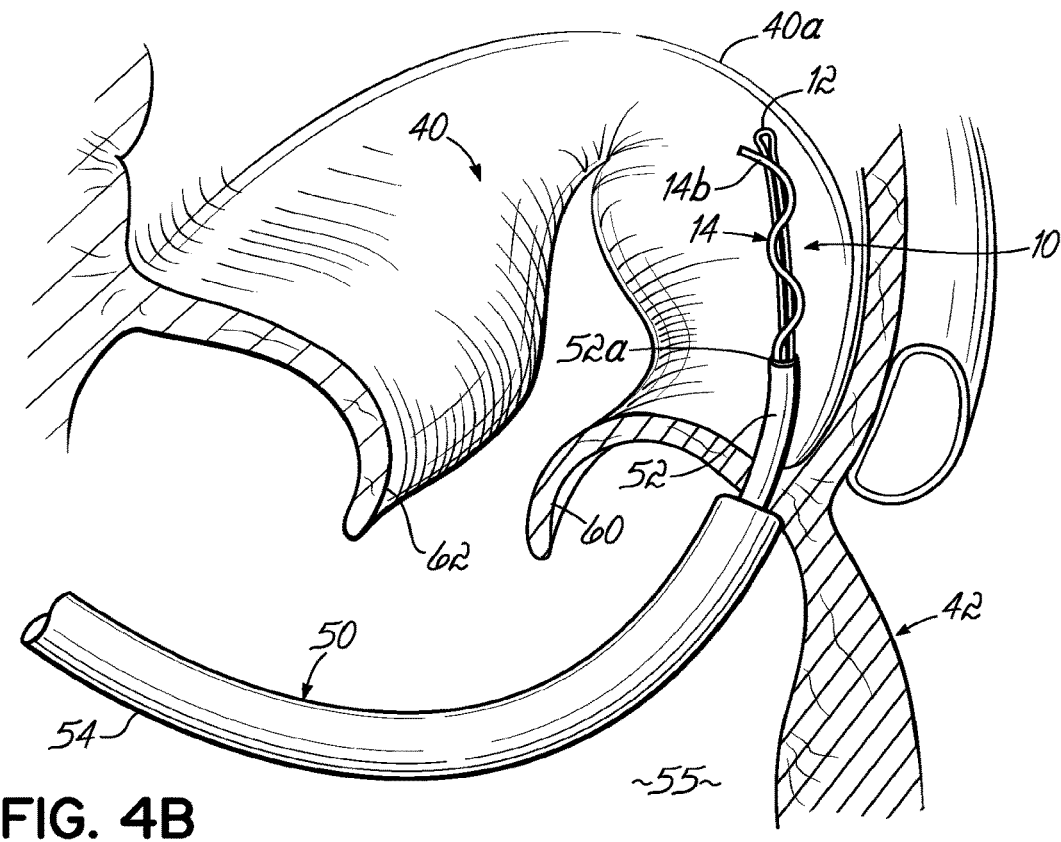
Figure 4C:
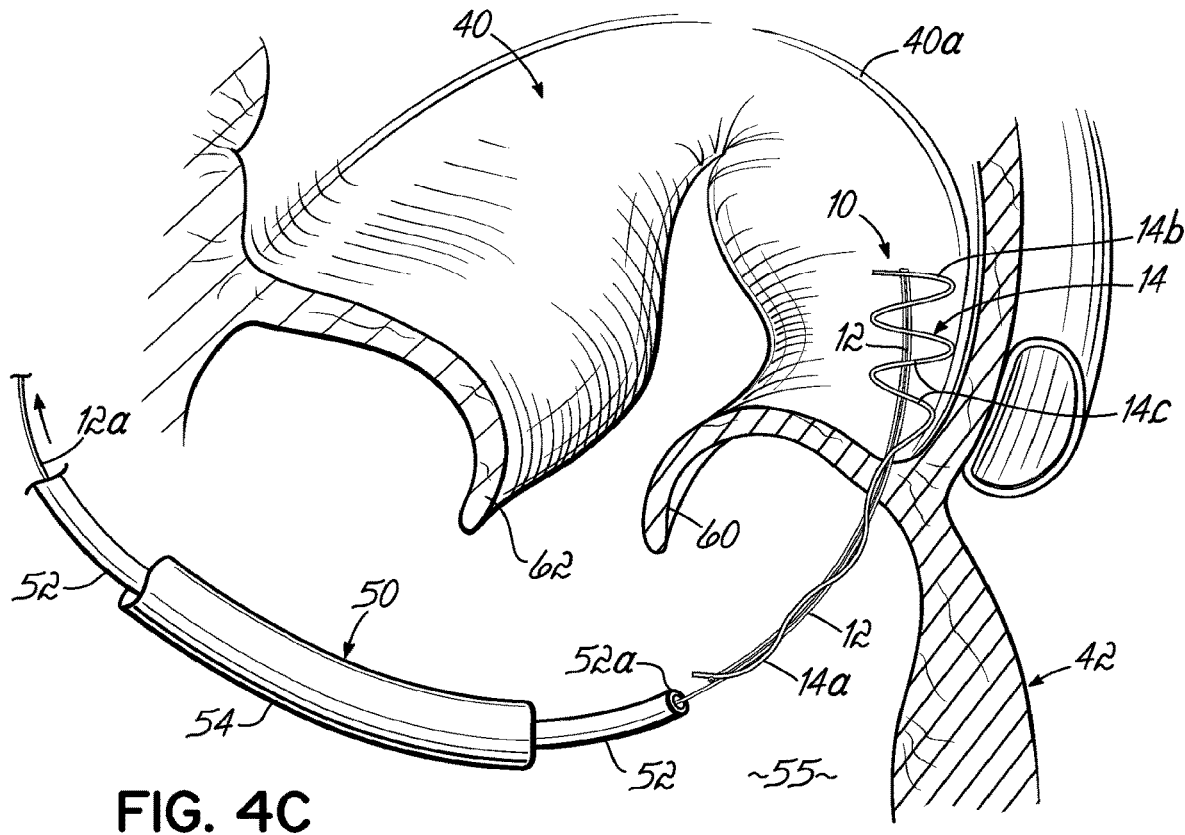
Figure 4D:
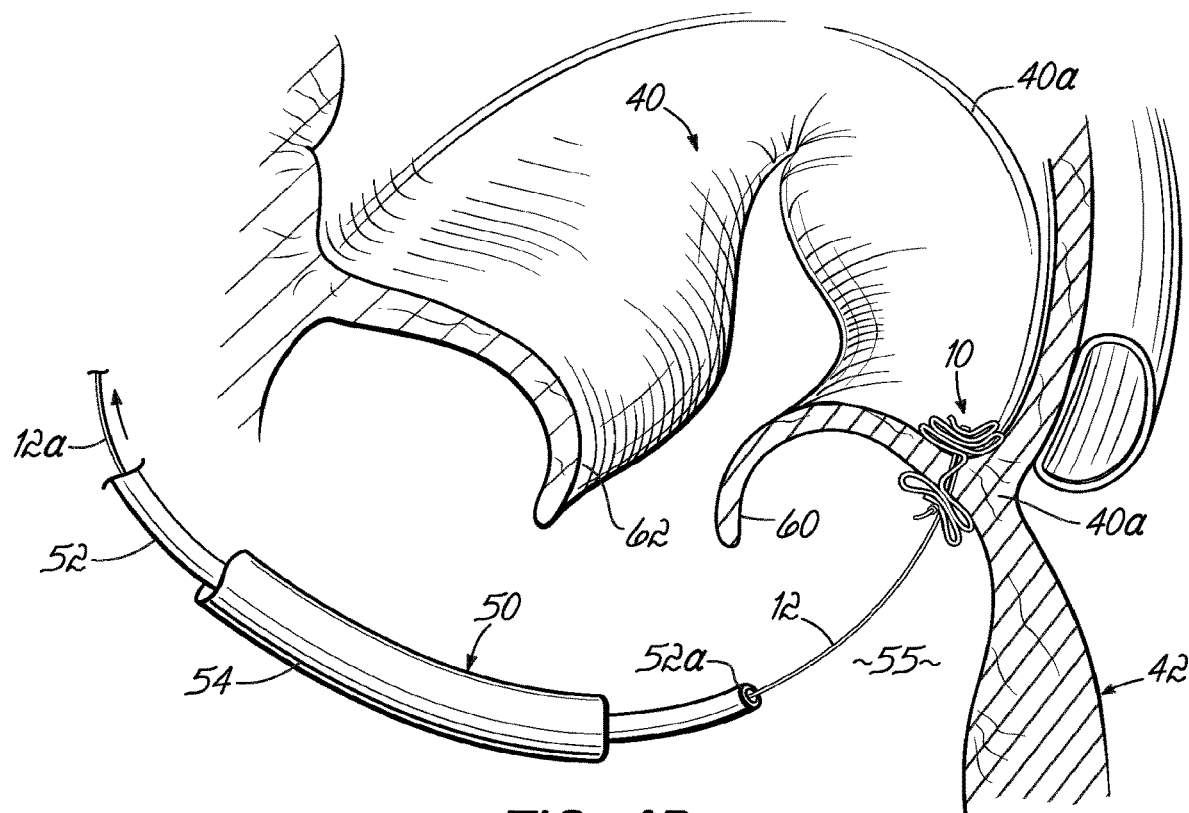

As illustrated in FIG. 4A, a first tissue anchor 10 is deployed through a catheter device 50 which may, for example, have an inner tubular member 52 or deploying catheter received within an outer tubular member 54 or delivery catheter. The tissue anchor 10 and tensioning member 12 are carried within the inner tubular member 52 and are deployed from a distal end 52a thereof. To ensure that proper force is applied to penetrate the tissue, tissue anchor 10 may be deployed or extended after the inner tubular member 52 has been inserted through tissue at the annulus 40a of the mitral valve 40. This is best illustrated in FIG. 4B. The inner tubular member 52 is withdrawn from the annulus tissue 40a either before, during or after activation of the distal end portion 14b of the elongate strip 14. As previously described, activating (e.g., compression, folding or otherwise shortening) the elongate strip 14 by pulling the suture 12 causes the distal end portion 14b and then proximal end portion 14a to be securely compressed and folded against opposite sides of the annulus tissue 40a. This procedure is repeated at least one additional time to securely fasten an additional tissue anchor 10 at a location spaced from the initial location. For example, the initial location may be at location P2 of the mitral valve annulus 40 while the second location may be spaced on either side of location P2. Catheter device 50 may be inserted into the location of annulus 40a in various manners, but is shown being inserted downwardly through the aortic valve 53 into the left ventricle 55, and curving upward toward the mitral valve annulus 40a.

Figure 4E:
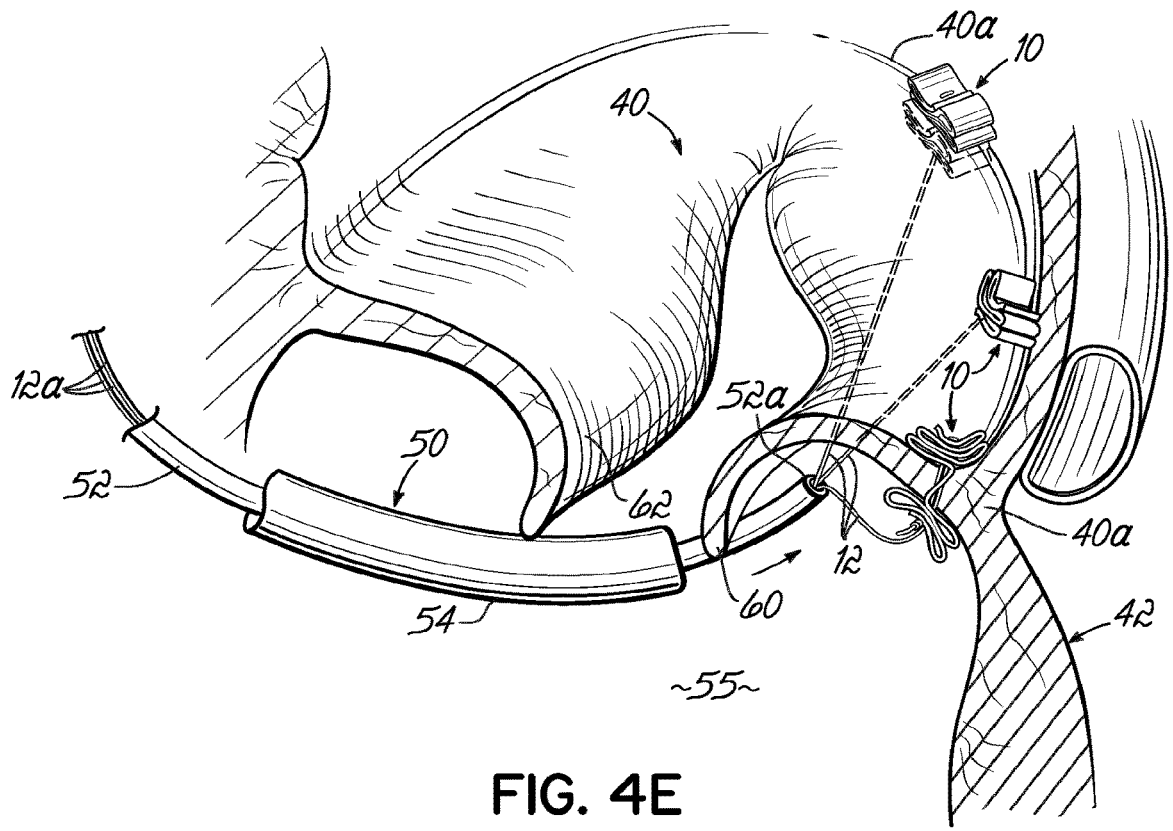
Figure 4F:
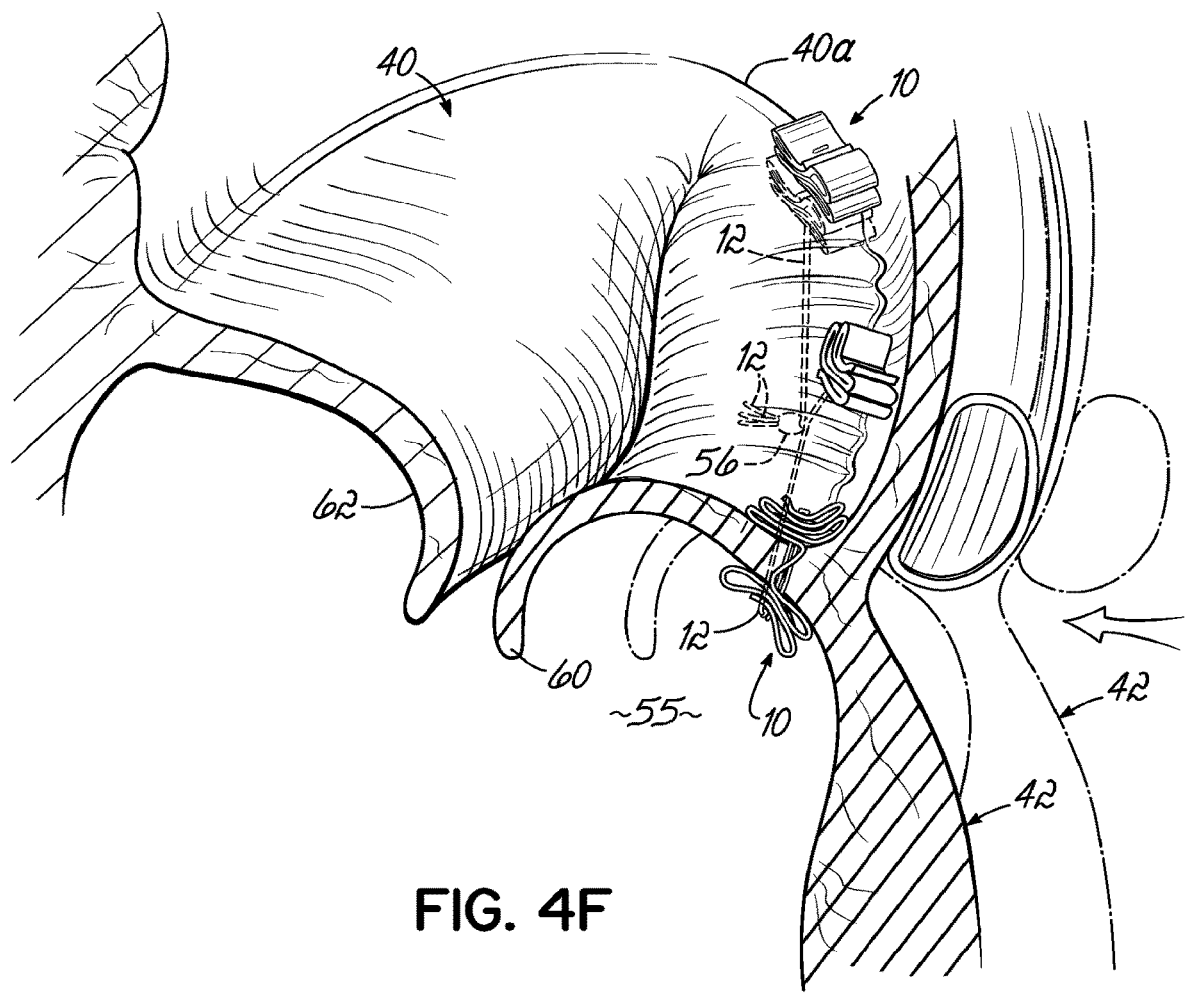

In the illustrative example shown in FIG. 4E, three tissue anchors 10 have been deployed and securely fastened to the annulus tissue 40a. As shown in FIG. 4F a suture locker 56 may then be deployed and used to maintain relative position and, therefore, tension between each of three respective tensioning members or sutures 12 associated with the three tissue anchors 10 after the tissue anchors 10 have been pulled closer to each other thereby plicating the tissue 40a between the anchors 10. This essentially shortens the valve annulus 40a and pulls the posterior leaflet 60 toward the anterior leaflet 62 to prevent leakage through the valve 40, i.e., to achieve better coaptation of the posterior and anterior leaflets 60, 62 during systole.

Figure 5A:
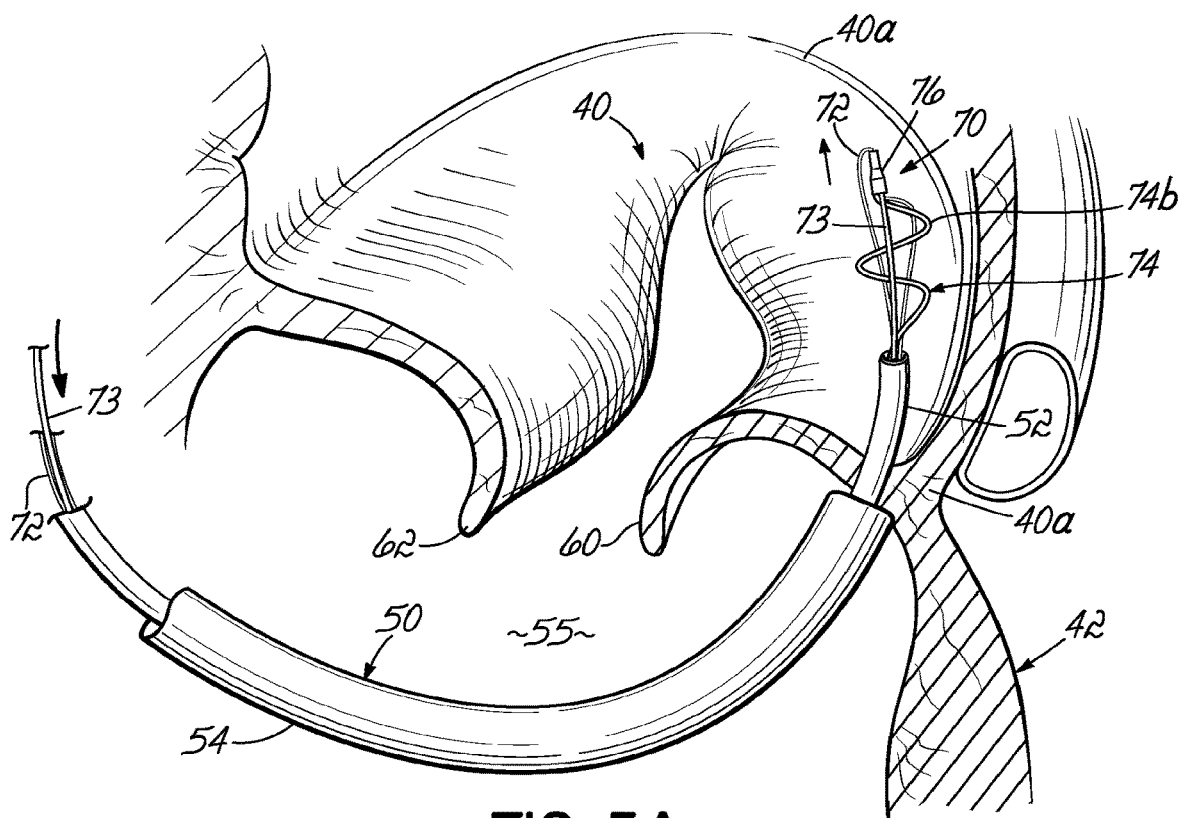
FIGS. 5A-5E are perspective views illustrating a mitral valve annuloplasty procedure utilizing tissue anchors constructed according to a second embodiment of the invention.
Figure 5B:
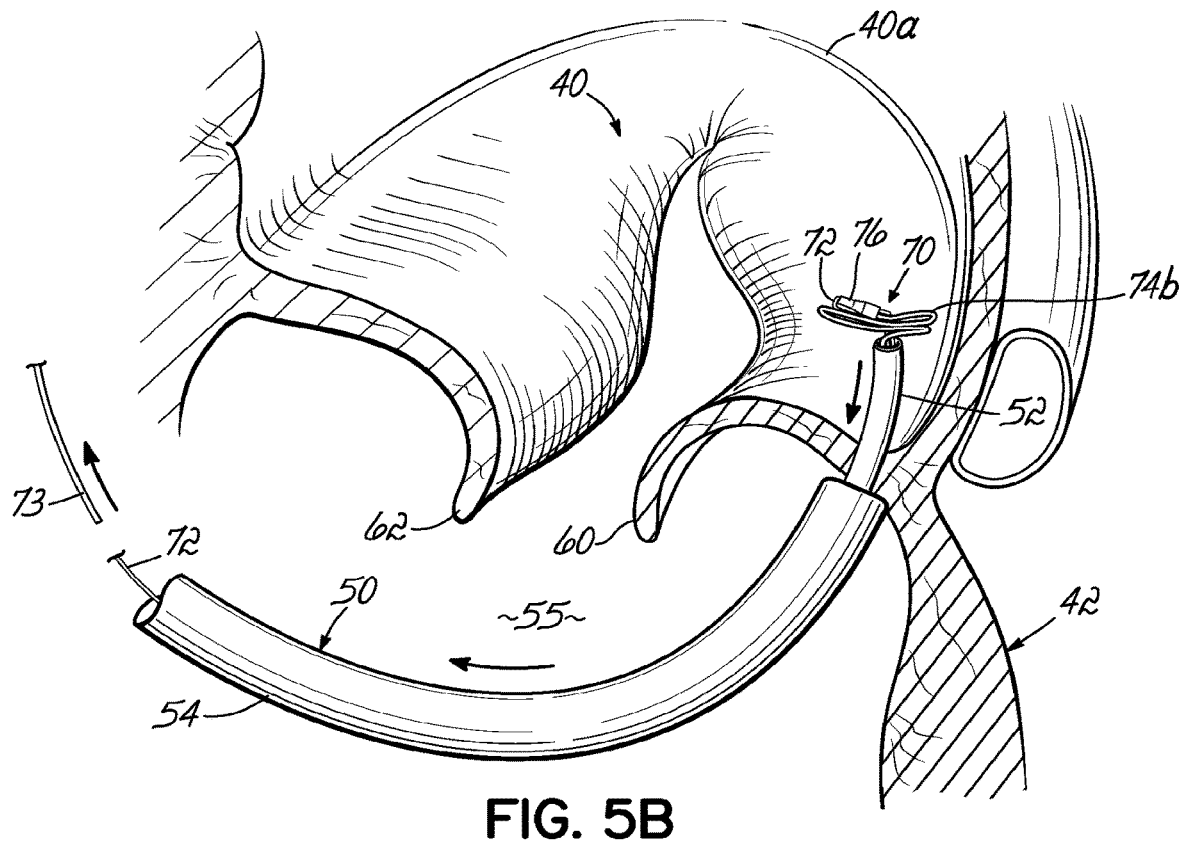
Figure 5C:
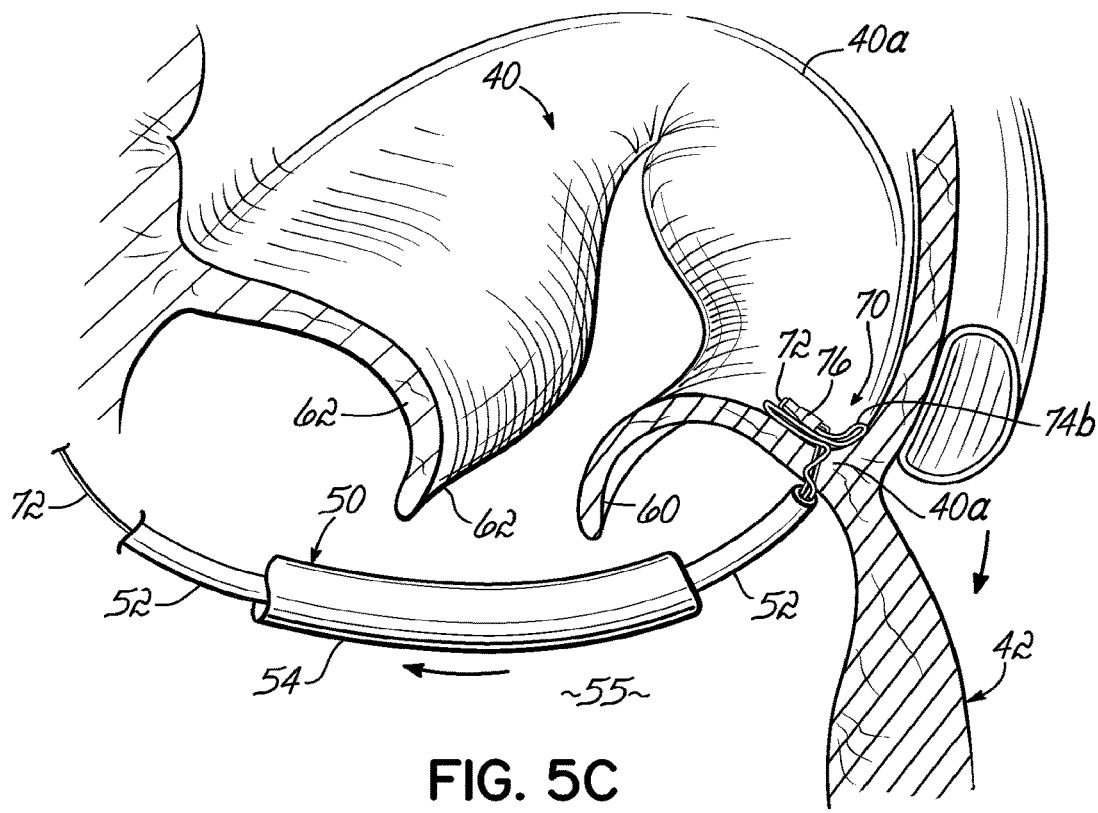
Figure 5D:
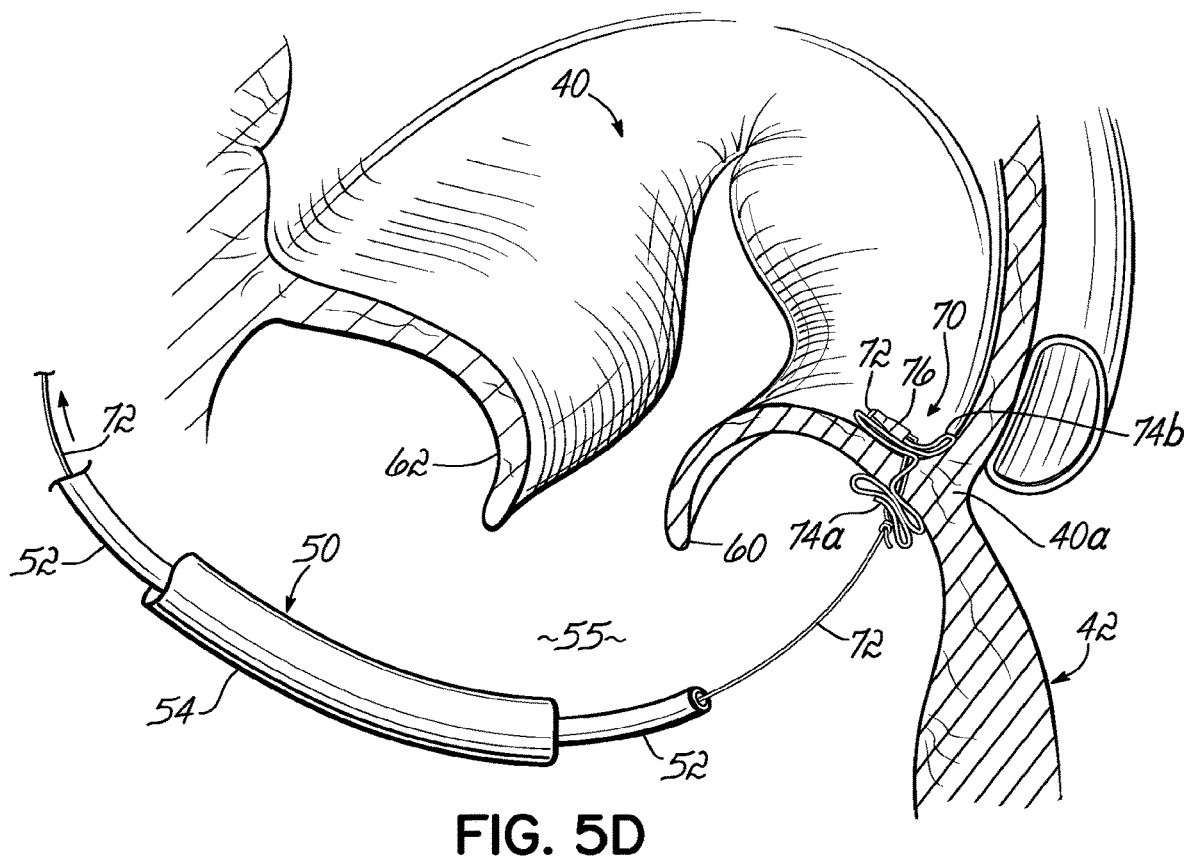
Figure 5E:
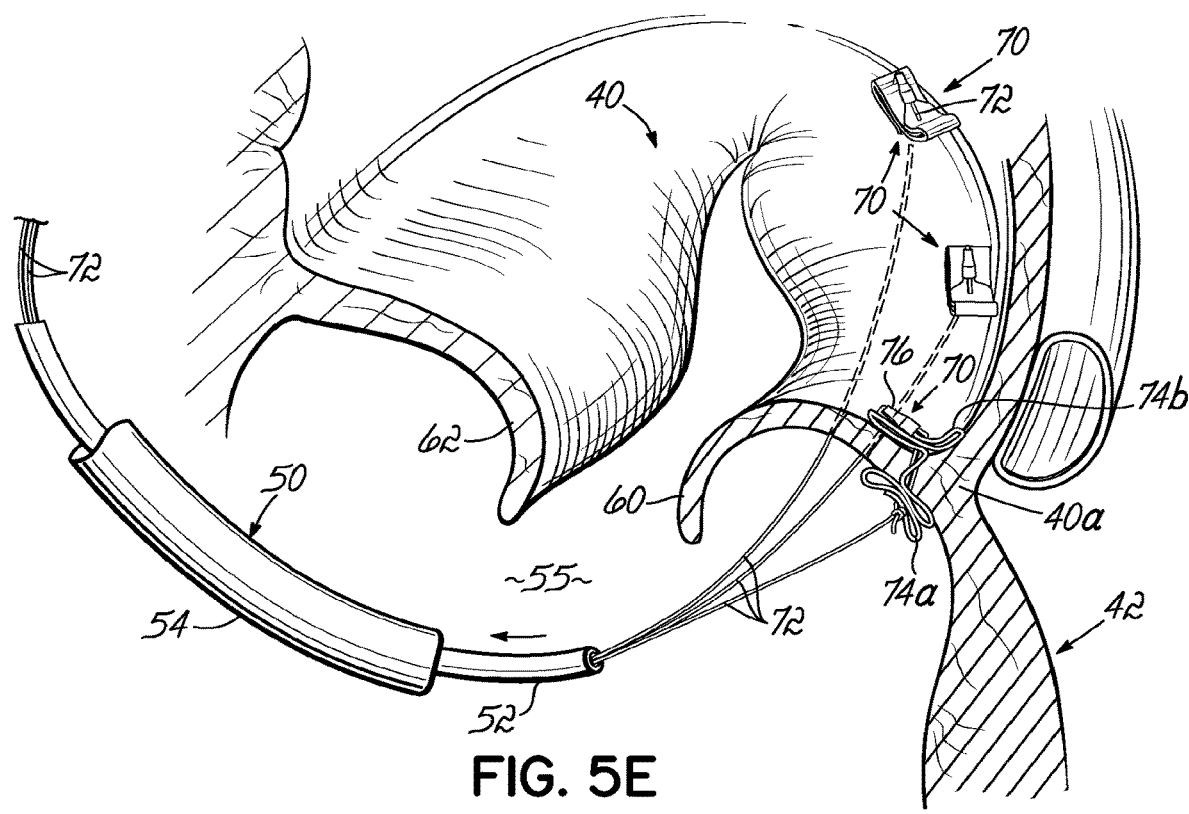

FIGS. 5A-5E illustrate a similar annuloplasty procedure on a mitral valve 40 utilizing a second embodiment of a tissue anchor 70 and a modified method of deployment and activation. In general, the differences between anchor 70 and anchor 10 will be described below with the understanding that all other attributes, options and features associated with anchor 70 may be as described above in connection with anchor 10. As shown in FIG. 5A, in this embodiment a tensioning member 72 is again used to activate a flexible, elongate flat strip 74 having proximal and distal end portions 74a, 74b. Strip 74 includes a tip 76 that is formed or otherwise secured on the distal end portion 74b. The tensioning member 72 and the tip 76 are arranged such that the tensioning member 72 slides relative to the tip 76. More particularly, the tensioning member 72 can be threaded through the tip 76. Tip 76 is made to be relatively rigid as compared to other flexible portions of strip 74 and of smaller diameter than the width of strip 74. Therefore, tip 76 helps to penetrate the annulus tissue 40a as the inner tubular member 52 and the elongate strip 74 are extended through the tissue 40a. A wire 73 may be used to push the tip 76 out of the tubular member 52 at the desired time. The tip 76 may protrude slightly from the inner tubular member 52 as the tissue 40a is penetrated to assist with piercing the tissue 40a. The tip 76 may also assist with forcing distal portion or half 74b of strip 74 into a folded or otherwise shortened configuration. To help prevent the distal portion 74b of the elongate strip from pulling back through the tissue 40a as the inner tubular member 52 is withdrawn from the annulus tissue 40a, the free end of the tensioning member 72 is pulled while the inner tubular member 52 is still penetrated through the tissue 40a and into the left atrium 80 from the left ventricle 55. This forms the distal portion 74b into a folded or otherwise shortened configuration as shown in FIG. 5B. The inner tubular member 52 may then be withdrawn without also withdrawing the elongate flexible strip 74 with it, as shown in FIG. 5C. The proximal portion 74a of the elongate strip 74 is then deployed by pulling the inner tubular member 52 further in a proximal direction, and thereby exposing the full length of strip 74. The tensioning member 72 is pulled or tensioned so as to draw and compress the proximal portion 74a of the elongate strip 74 into a folded, shortened condition against an underside of the annulus tissue 40a as shown in FIG. 5D. As with the previously described annuloplasty procedure using the first embodiment of the tissue anchor 10, this is repeated as many times as necessary to create the necessary number of tissue plications. FIG. 5E illustrates this by way of an exemplary view of three successive tissue anchor securement locations with tissue anchors 70 that may be drawn together and locked in place to achieve and retain the plications as described in connection with FIG. 4F. Such plications reduce or close the gap between the posterior and anterior leaflets 60, 62. during systole FIG. 6 is a side elevational view of the tissue anchor 70 as shown and described with respect to the annuloplasty procedure of FIGS. 5A-5E. This embodiment differs from the first embodiment in a number of different manners, in addition to the use of a distal tip 76 for tissue penetration purposes. For example, the elongate strip 74 is somewhat shorter than the elongate strip 14 utilized in the first embodiment. For example, the strip 74 may be about 40 mm long by about 3 mm wide. Of course, any other desired dimensions and shapes may be used depending on application needs. This may be desirable to achieve a lower profile deployed and fastened configuration with fewer folds that may lead to more versatile applications, lower incidents of blood clotting, easier use, etc. In addition, respective proximal and distal radiopaque bands 90, 92 are secured to the suture 72 at the proximal end portion of the strip 74 and to either the interior or exterior of the distal tip 76. Under a fluoroscope, these bands or other markers 90, 92 will indicate to the surgeon that the anchor 70 has been deployed, activated and fully compressed and/or fastened as necessary during the procedure. The tip 76 itself may alternatively be formed from a radiopaque material. In this second embodiment, the knot 94 formed in the suture 72 or other tensioning member is a slip knot through which another portion of the suture 72 slides during activation of the tissue anchor 70. It will be appreciated that this slip knot 94 may be replaced by another element which serves essentially the same purpose but takes the form, for example, of a small tubular element or other feature similar in function to a slip knot.

As further shown in FIGS. 6 and 7, the tensioning member or suture 72 can advantageously extend through respective fold portions 74c of the elongate strip 74 in essentially an hourglass configuration. Specifically, adjacent portions of the suture 72 located near the proximal and distal end portions 74a, 74b of the strip 74 are spaced farther apart than the adjacent portions of the suture 72 in the middle of the strip 74. As further shown in FIG. 7A, radiopaque markers, such as distinct areas of dots 95, may be used for enabling the surgeon to visualize the folds of the elongate strip 74 during deployment and securement of the elongate strip 74. These dots or other radiopaque markers may be printed on the strip 74. For example, dots 95 or other markers may be formed with a platinum powder base ink or other suitable material that is radiopaque and biologically compatible. This radiopaque material may also add stiffness to the fold sections 74c thereby helping to maintain the fold sections 74c flat and increasing retention force on the tissue. Meanwhile, the fold lines 74d between fold sections 74c can remain highly flexible to create tight radius fold lines. As further shown in FIG. 7, each of the holes 96 that the tensioning member or suture 72 is received through may be marked by circles 98 surrounding each hole 96 or other markers for visualizing purposes during assembly of the tensioning member or suture 72 with the elongate strip 74.

Figure 7B:
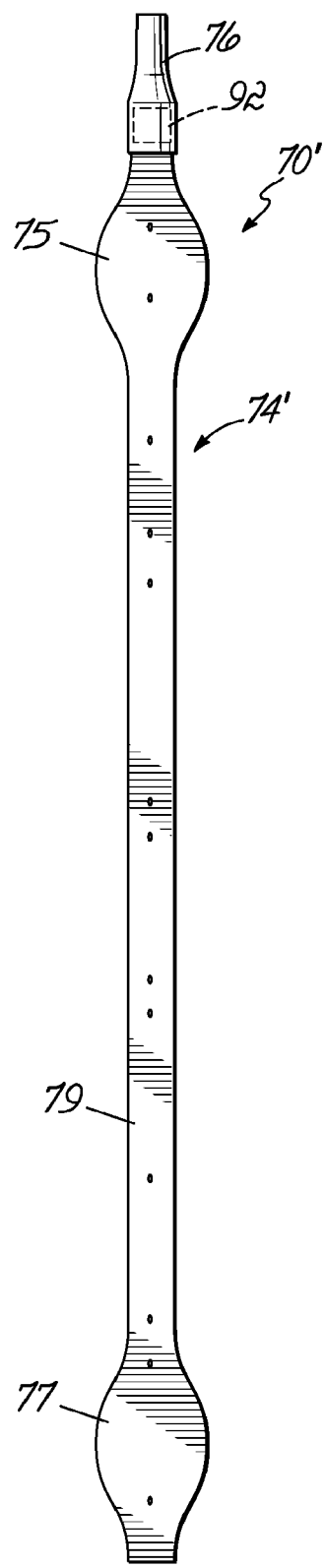
FIG. 7B is a front elevational view of an alternative anchor strip having a varying width along its length.
Figure 7C:
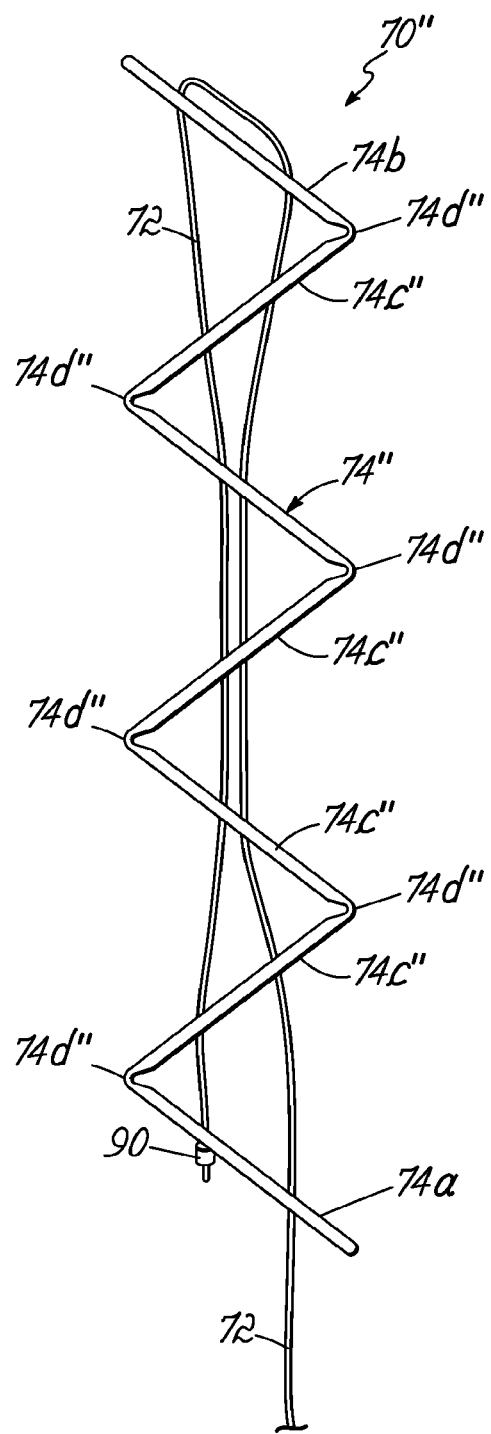
FIG. 7C is a side elevational view of another alternative anchor strip utilizing more rigid fold sections separated by living hinges.

Optionally, holes 96 may be eliminated and the suture 72 may be threaded with a needle through the strip 74. One could also, for example, choose different sets of holes 96 along strip 74 for receiving the tensioning member or suture 72 thereby changing the width of the folds and/or number of folds and/or shape of the folds depending on the application needs or desires of the surgeon. The tensioning member or suture 72 may be threaded or otherwise attached along the strip 74 in any number of manners including, for example, x-patterns or other crossing patterns, zig-zag patterns, etc. that may alter the folded or otherwise shortened or compressed footprint of the anchor into various beneficial shapes, such as flower shapes, circular shapes or other rounded shapes, ball shapes or other configurations. Modifications of the manner in which the tensioning member or suture 72 is threaded or otherwise attached along the length of strip 74 may result in higher or lower tensioning force being required to compress the anchor and/or higher or lower friction holding force that may help maintain the anchor in the compressed or shortened configuration. The width of the elongate strip 74' may be varied along its length, such as by tapering, stepping, or forming an hourglass shape or shapes along the length of the strip 14. For example, as illustrated in FIG. 7B, having proximal and distal end portions 75, 77 of wider dimension than an intermediate or middle portion or portions 79 along the length of strip 74' will allow these wider portions 75, 77 may cover over the more intermediate folded portions 79 and prevent unnecessary contact with adjacent tissue during use. It will be appreciated that like reference numerals are used herein to refer to like elements in all embodiments and reference numerals with prime marks (') or double prime marks (") refer to like elements that have been modified in a manner as described herein or otherwise shown in the associated figure. Strip 74 may have variable stiffness including, for example, a relatively rigid perimeter or relatively rigid edges 74e, 74f (FIG. 7) or intermittent relatively rigid sections 74c" separated by flexible sections such as living hinges 74d" (FIG. 7C) that may aid in folding and securing the elongate strip 74" into a folded condition.

Figure 8D:
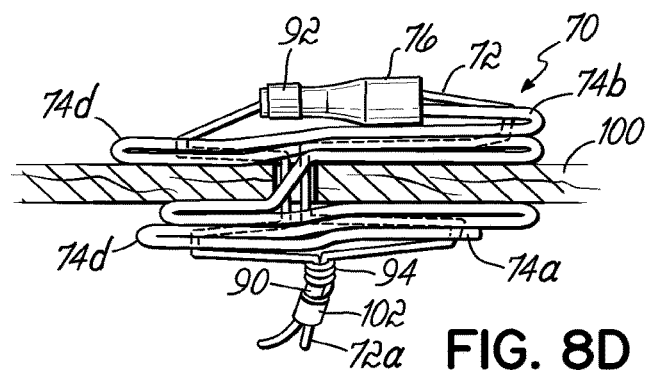
FIGS. 8A-8D are respective side views illustrating a sequence of steps used for securing the tissue anchor of the second embodiment to a layer of tissue.
Figure 8E:
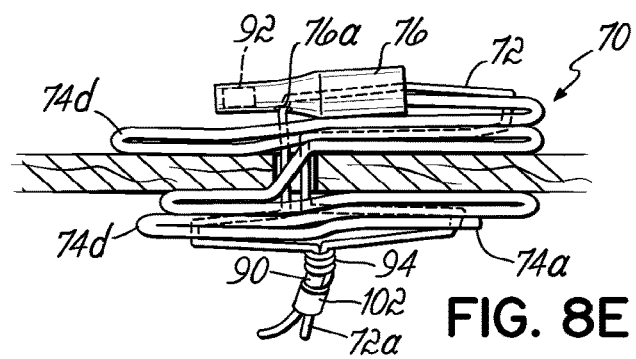
FIG. 8E is a view similar to FIG. 8D, but illustrating an alternative tip and tensioning member arrangement.
Figure 8C:
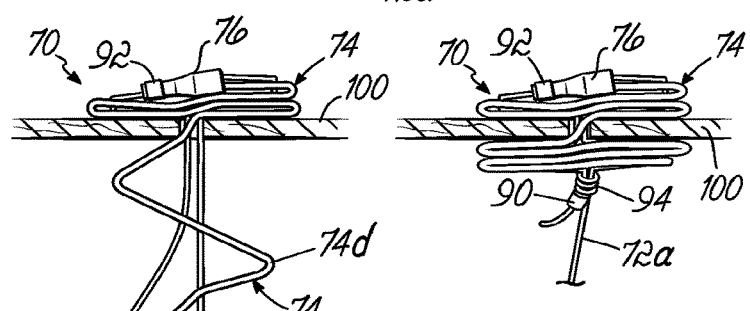
Figure 8A:
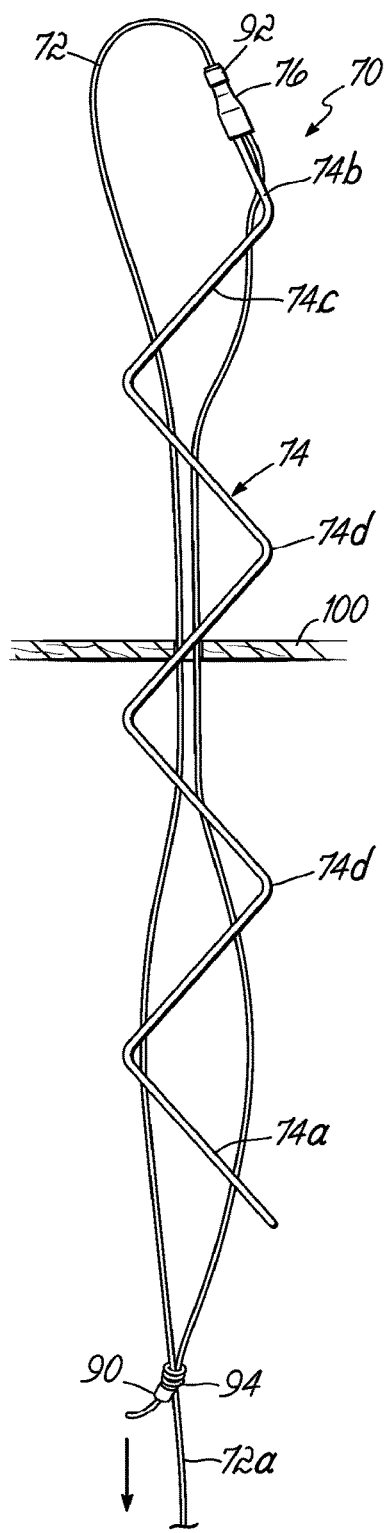
Figure 8B:
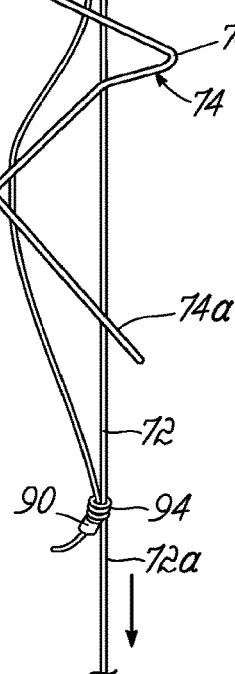

FIGS. 8A-8D illustrate a series of steps for deploying and securely fastening the tissue anchor 70 of the second embodiment to a layer of tissue 100. Generally, as shown in FIG. 8A, the combination of the elongate strip 74 and tensioning member or suture 72 is deployed through the layer of tissue 100. One end or portion 72a of the suture 72 that extends through the slip knot 94 is then pulled. This causes the distal portion 74b of the elongate strip 74 to fold and compress against the distal side of the tissue layer 100. As shown in FIG. 8B, further pulling of the tensioning member 72 causes the slip knot 94 to ride upwardly or distally along the suture 72 and against a proximal portion 74a of the elongate strip 74 thereby folding and compressing the proximal portion 74a against the proximal side of the tissue layer 100 as shown in FIG. 8C. As shown in FIG. 8D, a suitable crimp or locking element 102 may be used to securely lock the slip knot 94 in place relative to the suture or tensioning member segment which extends therethrough. This will lock the entire anchor 70 in place with the respective proximal and distal folded strip portions 74a, 74b securely retaining the tissue layer or layers 100 therebetween. FIG. 8D shows the tip 76 acting as a retainer on top of the distal end portion 74b to assist in holding the distal end portion 74b in place. FIG. 8E shows an alternative in which the tensioning member is threaded through at least one hole 76a more centrally located in the tip. Yet another alternative would be to thread the tensioning member through two centrally located holes instead of through the proximal end of the tip 76 and one centrally located hole 76a as shown in FIG. 8E. These alternatives allow the tip 76 to act more like a "T"-bar with forces acting in a more perpendicular or normal manner relative to the distal end portion 74b of the strip 74.

Figure 9A:
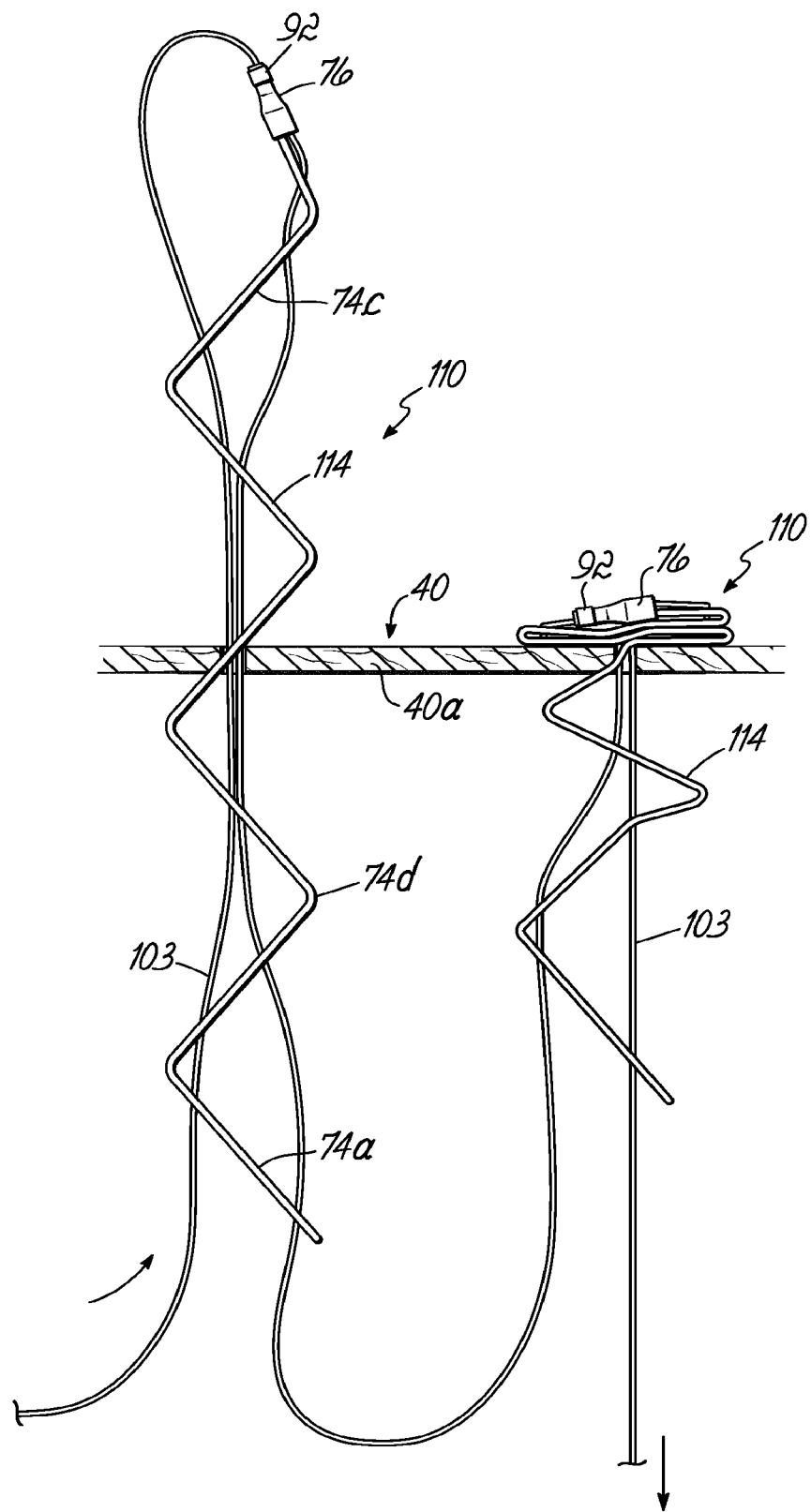
FIGS. 9A-9C are respective side elevational views illustrating an annuloplasty procedure in which two tissue anchors of the second embodiment are daisy-chained together with a single tensioning member to plicate the tissue between the anchors in a more integrated procedure.
Figure 9B:
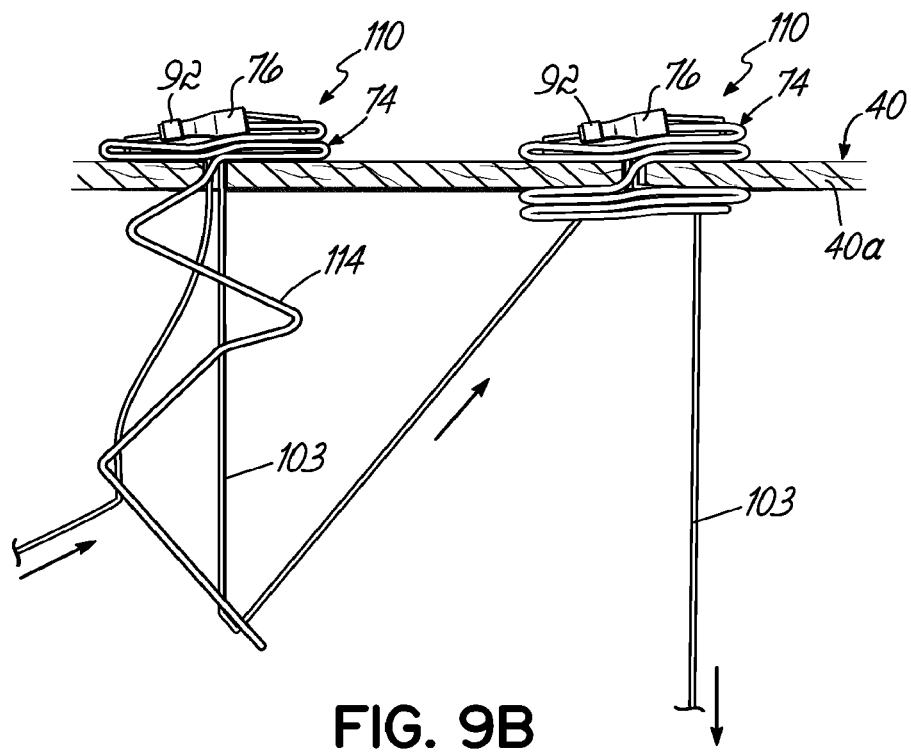
Figure 9C:
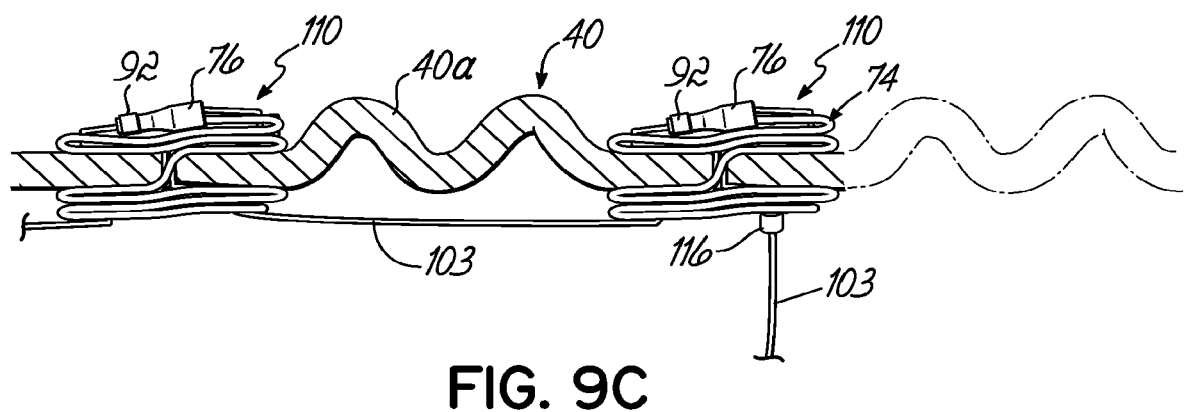

FIGS. 9A-9C illustrate another alternative embodiment of a plication procedure, for example, for use during annuloplasty on a mitral valve annulus 40a. In this regard, a single tensioning member, such as a suture 103 or other member may be used to deploy, fasten and draw together at least two separate tissue anchors 110. As shown in FIG. 9A, first and second tissue anchors 110 may be respectively deployed at spaced apart locations along the mitral valve annulus 40a. Each tissue anchor 110 includes an elongate strip 114 of flexible material, such as fabric or other material as described above, as well as a single suture 103 or tensioning member extending through each of the elongate strips 114. Upon deployment of the two tissue anchors 110 through the tissue layer 40 at spaced apart locations, the free end of the suture 103 or tensioning member is pulled thereby securely fastening the first tissue anchor 110 as shown in FIGS. 9A and 9B and subsequently securely fastening the second tissue anchor 110 to the annulus tissue 40a. Upon further pulling or tensioning of the suture 103, the tissue anchors 110 will be drawn together to plicate the tissue 40 therebetween as shown in FIG. 9C. A crimp or other locker member 116 may then be used to lock in the desired amount of plication by crimping onto the free end of the suture 103 adjacent to the slip knot 94 of the first tissue anchor 110 as shown in FIG. 9C. The free end of the suture 103 may then be cut to eliminate or reduce the length of the suture tail.

Figure 10A:
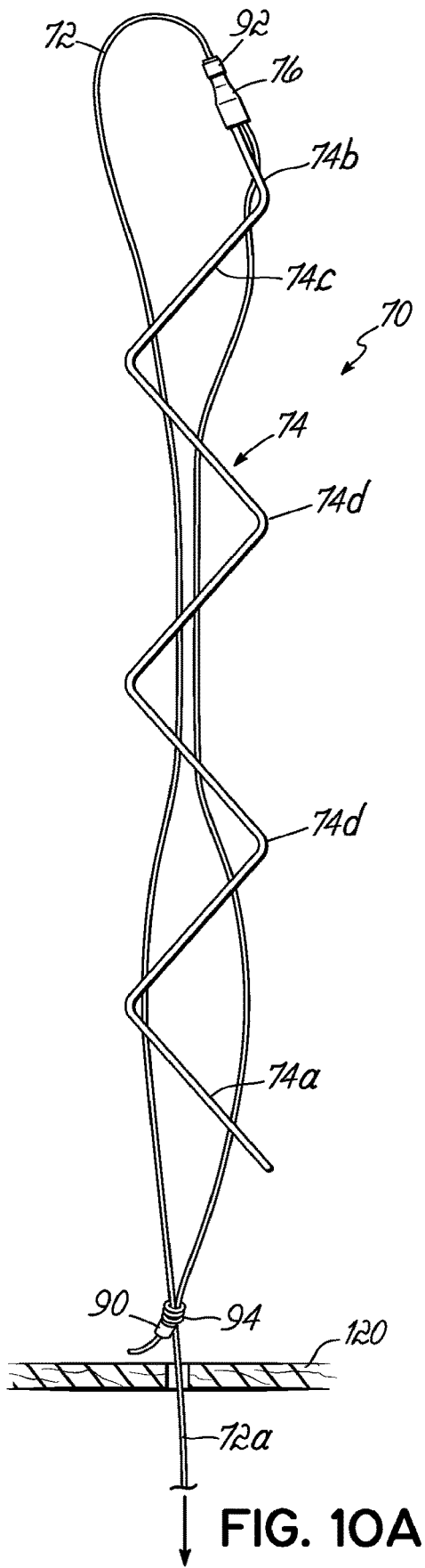
FIGS. 10A and 10B are respective side elevational views illustrating the tissue anchor of the second embodiment used to provide an anchor or securement location on only one side of a tissue layer.
Figure 10B:
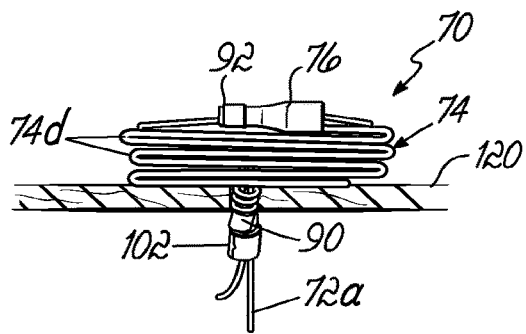

FIGS. 10A and 10B illustrate a tissue anchor 70 of the second embodiment, for example, being used to provide an anchor or securement location on only one side of a tissue layer 120. In this regard, the tissue anchor 70 may be extended entirely through the tissue layer(s) 120. The free end of the suture or tensioning member 72 is then pulled proximally to compress and fold the elongate strip 74 against the distal side of the tissue layer 120 as shown in FIG. 10B. It will be appreciated that activation of strip 74 occurs similarly to the other described embodiments, except that the activated portion (that is, the folded or otherwise shortened portion) is located entirely on one side of the tissue layer 120. As illustrated, the intermediate or middle portion between the proximal and distal end portions of the anchor member shortens to adjust to the amount of tissue contained therebetween (if any) or shortens during the compression process on only one side of the tissue.

While the present invention has been illustrated by a description of various illustrative embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in numerous combinations depending on the needs and preferences of the user.

What is claimed is:

1. An apparatus for use with tissue of an annulus of a heart valve of a subject, the apparatus comprising an annuloplasty implant that comprises:

an elongate fabric member configured to be anchored to the tissue, and to move between an elongate configuration and a shortened configuration, the fabric member having a first end portion, a second end portion, and a compressible intermediate portion between the first end portion and the second end portion; and a tensioning member:
having a first tensioning-member end and a second tensioning-member end,
defining a first segment and a second segment by being turned back on itself at a turn such that (i) the first segment extends between the first tensioning-member end and the turn, (ii) the second segment extends between the turn and the second tensioning-member end, and (iii) the second segment is alongside the first segment, and
operatively connected to the fabric member by the first segment and the second segment being threaded, along the fabric member and alongside each other, between the first end portion and the second end portion, such that the fabric member can slide relative to the tensioning member, wherein:
the turn of the tensioning member is disposed at the second end portion of the fabric member,
the operative coupling of the tensioning member to the fabric member is such that tensioning of the tensioning member causes the fabric member to move from the elongate configuration to the shortened configuration by the tensioning member (i) pulling both the first end portion and the second end portion toward the intermediate portion, and (ii) compressing the intermediate portion, and
the implant is configured to reshape the annulus of the heart valve.

2. The apparatus according to claim 1, wherein the fabric member is formed from a material selected from at least one of: natural fibers, synthetic fibers, polymers, and metals.

3. The apparatus according to claim 2, wherein the tensioning member further comprises a suture.

4. The apparatus according to claim 1, wherein the tensioning member further comprises a suture.

5. The apparatus according to claim 1, wherein the tensioning member includes a stop member engageable with the fabric member.

6. The apparatus according to claim 5, wherein the stop member further comprises a knot in the tensioning member.

7. The apparatus according to claim 1, wherein the tensioning member extends through the fabric member at multiple locations between the first end portion and the second end portion.

8. The apparatus according to claim 1, wherein the fabric member and the tensioning member are configured such that the fabric member forms at least one fold upon pulling the first tensioning-member end.

9. The apparatus according to claim 1, further comprising a lock member engageable with the tensioning member to retain the fabric member in the shortened configuration.

10. The apparatus according to claim 1, further comprising at least one radiopaque marker on at least one of the fabric member and the tensioning member.

11. The apparatus according to claim 1, further comprising a first radiopaque marker located proximate the first end portion of the fabric member is in the shortened configuration and a second radiopaque marker located proximate the second end portion when the fabric member is in the shortened configuration.

12. The apparatus according to claim 1, wherein the implant comprises a tip at the second end portion, the tip being narrower and more rigid than the fabric member.

13. The apparatus according to claim 12, wherein the tip acts as a compressive force applying member against the second end portion of the fabric member when the fabric member is in the shortened configuration.

14. The apparatus according to claim 1, wherein the fabric member varies in width along its length when in the elongate configuration.

15. The apparatus according to claim 1, wherein the fabric member includes an edge portion that is more rigid than a central area of the fabric member.

16. The apparatus according to claim 1, wherein at least the first tensioning-member end is disposed at the first end portion of the fabric member.

17. The apparatus according to claim 1, further comprising a catheter device, wherein the annuloplasty implant is configured to be transluminally delivered to the heart valve through the catheter device, with the second end portion distal to the first end portion, such that deployment of the annuloplasty implant from the catheter device exposes the second end portion prior to the first end portion.

18. The apparatus according to claim 1, further comprising a catheter device configured to facilitate securing of the second end portion to the tissue, and to facilitate securing of the first end portion to the tissue subsequently to the securing of the second end portion to the tissue.

19. A system for use with tissue of an annulus of a heart valve of a subject, the system comprising:
an annuloplasty implant that comprises:
an elongate fabric member configured to be anchored to the tissue, and to move between an elongate configuration and a shortened configuration, the fabric member having a first end portion, a second end portion, and a compressible intermediate portion between the first end portion and the second end portion; and
a tensioning member having a first tensioning-member end and a second tensioning-member end, defining a first segment and a second segment by being turned back on itself at a turn such that (i) the first segment extends between the first tensioning-member end and the turn, (ii) the second segment extends between the turn and the second tensioning-member end, and (iii) the second segment is alongside the first segment, and operatively connected to the fabric member by the first segment and the second segment being threaded, along the fabric member and alongside each other, between the first end portion and the second end portion, such that the fabric member can slide relative to the tensioning member; and
a catheter device configured to facilitate securing of the second end portion to the tissue, and to facilitate securing of the first end portion to the tissue subsequently to the securing of the second end portion to the tissue;
wherein the turn of the tensioning member is disposed at the second end portion of the fabric member, the operative coupling of the tensioning member to the fabric member is such that tensioning of the tensioning member causes the fabric member to move from the elongate configuration to the shortened configuration by the tensioning member (i) pulling both the first end portion and the second end portion toward the intermediate portion, and (ii) compressing the intermediate portion, and the implant is configured to reshape the annulus of the heart valve.

* * * * *